US006623980B1

(12) United States Patent
Fisher et al.

(10) Patent No.: US 6,623,980 B1
(45) Date of Patent: Sep. 23, 2003

(54) EXO1 AND EXO2, EXOCYTOTIC PROTEINS

(75) Inventors: Joseph Fisher, San Carlos, CA (US); James Lorens, Menlo Park, CA (US); David Anderson, San Bruno, CA (US); Ying Luo, Los Altos, CA (US); Chao Bai (Betty) Huang, San Leandro, CA (US); Mary Shen, Newark, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 09/255,920

(22) Filed: Feb. 23, 1999

Related U.S. Application Data

(60) Provisional application No. 60/086,650, filed on May 26, 1998, and provisional application No. 60/075,534, filed on Feb. 23, 1998.

(51) Int. Cl.$^7$ .................. G01N 33/566; G01N 33/534; C12P 21/06; C12N 5/00; C12N 5/06; A61K 38/30; C07H 21/02
(52) U.S. Cl. ................. 436/501; 435/69.1; 435/325; 435/357; 436/518; 530/300; 536/23.1
(58) Field of Search ............................... 435/69.1, 325, 435/357; 436/518; 536/23.1, 23.5, 24.1

(56) References Cited

U.S. PATENT DOCUMENTS

| 5,663,315 A | * 9/1997 | Scheele et al. ............ 536/23.5 |
| 5,843,717 A | * 12/1998 | Hillman et al. ............ 435/69.1 |

FOREIGN PATENT DOCUMENTS

| WO | 97/28262 | 8/1997 |
| WO | 98/42839 | 10/1998 |

OTHER PUBLICATIONS

Knochel M et al, "Annexins in Paramecium cells", Histochemistry Cell Biol, 1996, 105:269–281.*
Bonnema JD et al, "Cytokine–enhanced NK cell–mediated cytotoxicity", Journal of Immunology, vol.152, No.5, Mar. 1, 1994, pp. 2098–2104.*
Kaether et al., "Targeting of green fluorescent protein to neuroendocrine secretory granules: A new protein to neuroendocrine secretion," European Journal of Cell Biology, Oct. 1997, vol. 74, No. 2, pp. 133–142.*
Iyer et al., "Quod erat demonstrandum? The mystery of experimental validation of apparently erroneous computational analysis of protein sequences," Genome Biology, 2001, vol. 2, No. 12, pp. 1–11.*
Wager et al., Molecular Cloning of a New Member of the Rab Protein Family, Rab26, from Rat Pancreas, Biochemical and Biophysical Research Communications, 1995, vol. 297, No. 3, pp. 950–956.*
Fernandez et al., "Capacitance measurements reveal stepwise fusion events in degranulating mast cells," *Nature*, 312:453–455 (Nov. 1984).

Zerial et al., "Rab GTPases in vesicular transport," *Curr. Opin. Cell. Biol.*, 5:613–620 (1993).
Lledo et al., "Rab3 proteins: key plays in the control of exocytosis," *TINS*, 17:426 (Nov. 1994).
Roa et al., *J. Immunol.*, "Involvement of the ras–Like GTPbases rab3d in RBL–2H3 Mast Cell Exocytosis Following Stimulation via High Affinity Ige Recepters (FcERi)[1]," 159:2815–2823 (1997).
Perou et al., "The Beige/Chediak–Higashi Syndrome Gene Encodes a Widely Expressed Cytosolic Protein," *J. Biol. Chem.*, 272:(47)29790–29794 (1997).
Barbosa et al., "Identification of the homologous beige and Chediak–Higashi syndrome genes," *Nature*, 382:262–265 (Jul. 1996).
Araki et al., "Inhibition of the Binding of SNAP–23 to Syntaxin 4 by Munc 18c," Biochemical and Biophysical Communications, 234:257–262 (1997).
Holz et al., "Evidence for the involvement of Rab3A in Ca2+–dependent Exocytosis from Adrenal Chromaffin Cells," The Journal of Biological Chemistry, 269(14):10229–10234 (1994).
Johannes et al., "The GTPase Rab3a negatively controls calcium–dependent exocytosis in neuroendocrine cells," The EMBO Journal, 13(9):2029–2037 (1994).
Katz et al., "Mouse mast cell gp49B1 contains two immunoreceptor tyrosine–based inhibition motifs and suppresses mast cell activation when coligated with the high–affinity Fc receptor for IgE," Proc. Natl. Acad. Sci. USA, 93:10809–10814 (1996).
McMahon et al., "The Novel ATM–Related Protein TRRAP is an Essential Cofactor for the c–Myc and E2F Oncoproteins," Cell, 94:363–374 (1998).
Oyama et al., "Two Distinct Anti–allergic Drugs, Amlexanox and Cromolyn, Bind to the Same Kinds of Calcium Binding Proteins, except Calmodulin, in Bovine Lung Extract," Biochemical and Biophysical Research Communications, 240:341–347 (1997).

(List continued on next page.)

Primary Examiner—Kenneth R. Horlick
Assistant Examiner—Young Kim
(74) Attorney, Agent, or Firm—DeAnn F. Smith; Megan E. Williams. Esq.; Lahive & Cockfield, LLP

(57) ABSTRACT

The present invention is directed to novel exocytotic polypeptides, such as Exo1 and Exo2 polypeptides and related molecules, which have an inhibitory effect on exocytosis and to nucleic acid molecules encoding those polypeptides. Also provided herein are vectors and host cells comprising those nucleic acid sequences, chimeric polypeptide molecules comprising the polypeptides of the present invention fused to heterologous polypeptide sequences, antibodies which bind to the polypeptides of the present invention and to methods for producing the polypeptides of the present invention. Further provided by the present invention are method for identifying novel compositions which mediate exocytotic polypeptide bioactivity, and the use of such compositions in diagnosis and treatment of disease.

12 Claims, 12 Drawing Sheets

OTHER PUBLICATIONS

Tellam et al., "Molecular Identification of Two Novel Munc–18 Isoforms Expressed in Non–neuronal Tissues," The Journal of Biological Chemistry, 270(11):5857–5863 (1995).

Wagner et al., "Molecular Cloning of a New Member of the RAB Protein Family, RAB 26, from Rat Pancreas," Biochemical and Biophysical Research Communications, 207(3):950–956 (1995).

* cited by examiner

```
1/1                                                                              31/11
ATG TTG AAG GAG TCC CAG AAG CTG CAC TAT GTT GTG ACT GAA GTT CAA GGC CCC AGC AAT
 M   L   K   E   S   Q   K   L   H   Y   V   V   T   E   V   Q   G   P   S   N
61/21                                                                            91/31
ACC GTG GAG TTC TCT GAT TGC AAA GCT TCT CTC CAG CTT CCG ATG GAA AAG GCC ATT GAG
 T   V   E   F   S   D   C   K   A   S   L   Q   L   P   M   E   K   A   I   E
121/41                                                                           151/51
ACC GCC CTG GAC TGC CTG AAA AGT GCC AAC ACA GAG CCC TAC TAC CGG AGG CAG GCA TGG
 T   A   L   D   C   L   K   S   A   N   T   E   P   Y   Y   R   R   Q   A   W
181/61                                                                           211/71
GAG GTG ATC AGG TGC TTC CTG GTA GCC ATG ATG AGC CTG GAG GAC AAC AAG CAT GCG CTT
 E   V   I   R   C   F   L   V   A   M   M   S   L   E   D   N   K   H   A   L
241/81                                                                           271/91
TAC CAG CTG CTG GCG CAC CCC AAC TTT ACA GAA AAG ACC ATT CCC AAT GTC ATC ATA TCA
 Y   Q   L   L   A   H   P   N   F   T   E   K   T   I   P   N   V   I   I   S
301/101                                                                          331/111
CAT CGC TAC AAA GCA CAG GAC ACT CCA GCC CGG GAC TCA CGC GGC CGC TCG ACG ATA
 H   R   Y   K   A   Q   D   T   P   A   R   D   S   R   G   R   S   T   I   K  STOP
```

ROUND 0
DMSO
IONOMYCIN

NUMBER $10^1$  $10^2$  $10^3$  $10^4$
FL3 -->

FIG._2B

ROUND 1
ROUND 0
IONOMYCIN

NUMBER $10^1$  $10^2$  $10^3$  $10^4$
FL3 -->

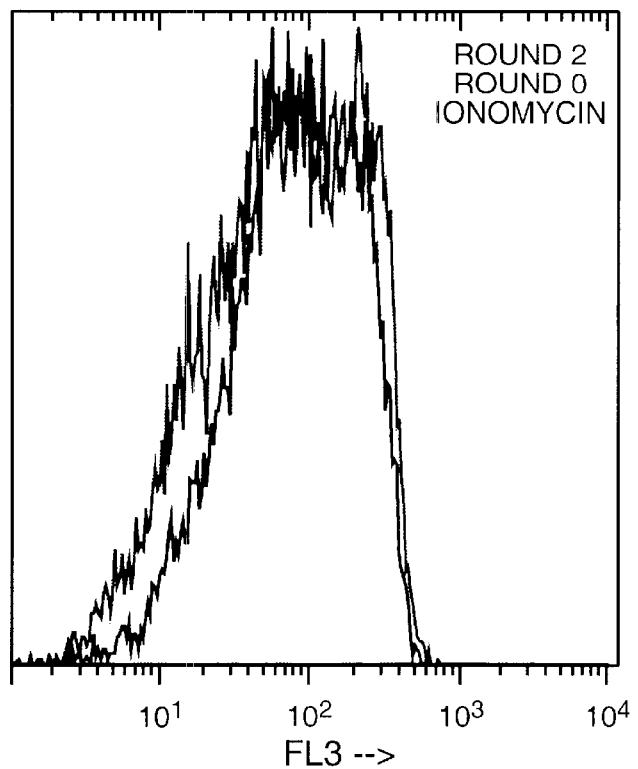
FIG._2C
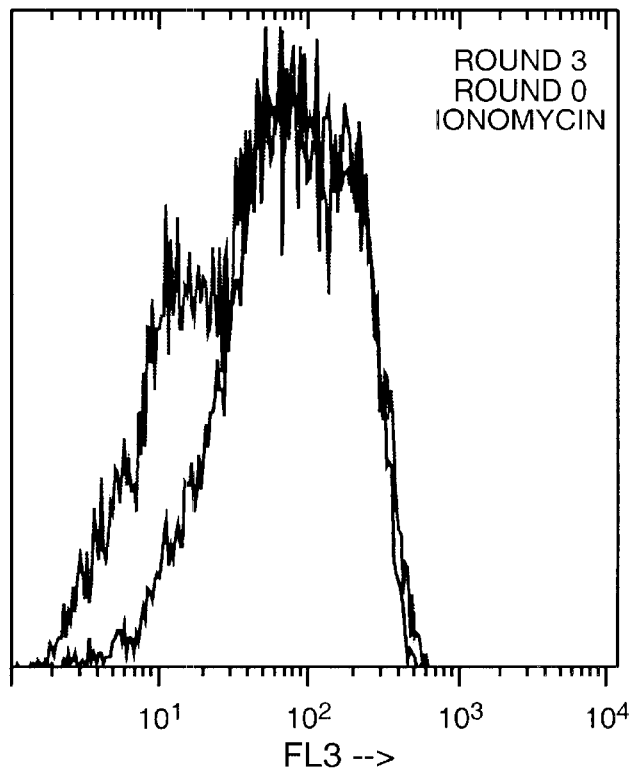
FIG._2D

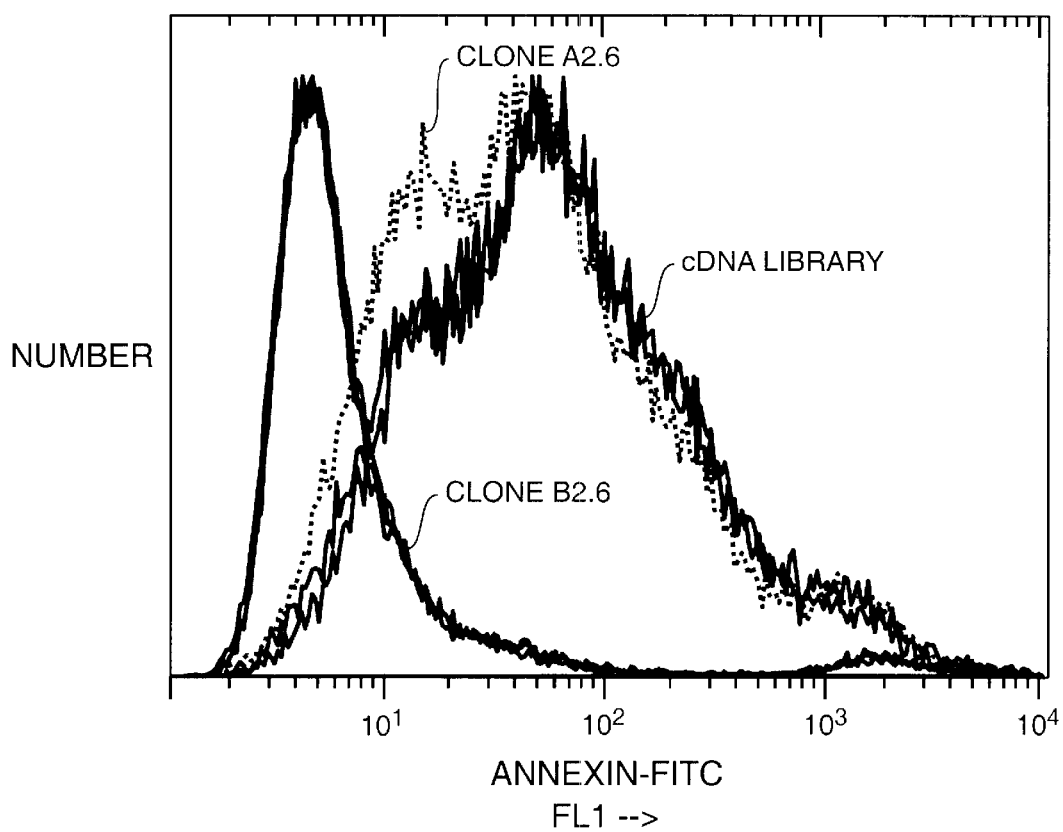

FIG._3

Clone B2.6 is Homologous to the Chediak-Higashi Syndrome Protein

Primary Sequence Homology

```
B2.6  14   EVQGPSITVEFSDCKASLQLP |MEKAIETALDCL| KSANTEPYYRRQA |WEVIRC| FL
CHp  384   EVQEDFVFSKYRHRALLLPEL |LEGVLQILICCL| QSAASNPFYFSQA |MDLVQE| FI
```

FIG._4A

Clone B2.6 is Homologous to the Chediak-Higashi Syndrome Protein

Secondary Structural Prediction

```
B2.6  ------- EEEE-----------HHHHHHHHHHHH-------------HHHHHH--
CHp   -----HHH-H-HH--H--HHHHHHHHHHHHHHH--------H----HHHHHH--
```

FIG._4B

CHEDIAK-HIGASHI
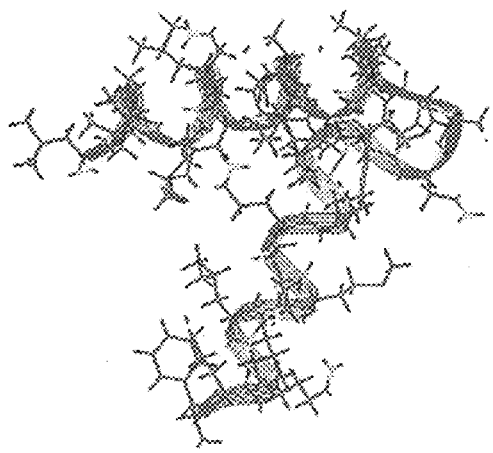
LEGVLQLLISCLQSAASNPFYFSQAMDLVQEF
EXO CLONE B26
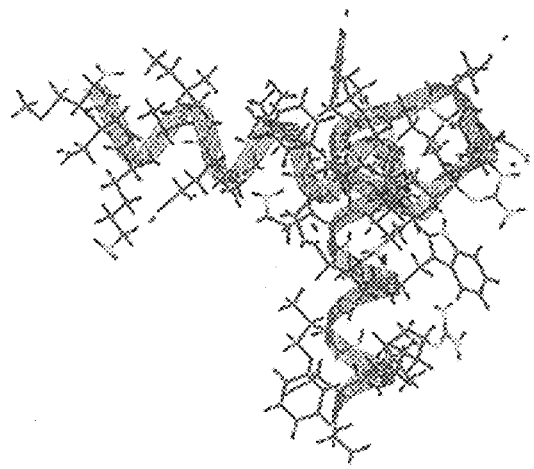
MEKAIETALDCLKSANTEPYYRRQAWEVIRCF
FIG._5

Rab26 Homolog 3' End Sequencing GAL4 AD Primer

```
AANCCNNNTAGNANNGNNCGGNGANATGAATGGCACACCAGGAGCTTGCTACCGCTTGGGGA
TGGCGAGGCCCTGAGCGCTCCCCGCCCTTCAGCCCGAACTACGATNTCACCGGCAAGGTGAT
GCTTCTTGGAGANTCGGGCGTCGGCAAAACCTGTTTCCTGATCCAATTCAAAGACGGGGCCTT
CCTGTCCGGAACCTTNATAGCCACCGTCGGCATAGACTTCAGGAATAAAGTGGTGACAGTGGA
TGGTTCCAGGGTGAAGCTTCAGATGCTTGGGACACTGCAGGACAGGAGCGCTTCCGCAGTGAC
CCATGCTTATTACCGAGATGCCCTGGCTCACAGAGATTCATGAGTATGCCCAGAGGACGTGGTGATT
TTTGACAACATCAGGGCCTGATGTAAGCAGCAGAAAGGGTGATCCGTTCTGAAGATGGAGA
ATGCTTCTAGGCAACAAGGCCGATGTGTTCCTTTCATGGAGACCAGTGCCAAGACTGCATGAACGT
GACACTGGCCAGGAATATGGTGTTCCTTTCATGGAGAACTGAAATACCGTGCAGGAGGCAGCCTGATGA
GGAGTTGGCCTTTCTGGCAATTGCCAAGAACTGAAATACCGTGCAGGAGGCAGCCTGATGA
GCCCAGCTTCCAGATCCGAGATCTGGAGTCCCAGAAGAAGCGCTCCAGCTGCTGCTCCTT
TGTGTGACCCCCTAGGGCTAAGAGGAGGGCTCAATGGGCAGCCCTGCCAAGGAGTAGCCATTA
CCACACCAACTAGGAGAAGCTGGGGGCTCAATGGGCAGCCCCTGCCAAGGAGTAGCCATTA
CCCTANGTTCTTTAGCTTCCCTGCA
```

FIG._6

```
Query:  124  MLLGXSGVGKTCFLIQFKDGAFLSGTXIATVGIDFRNKVVTVDGSRVKLQIWDTAGQERF  303
             ML+G  SGVGKTC L++FKDGAFL+GT  I+TVGIDFRNKV+ VDG +VKLQIWDTAGQERF
Sbjct:  1    MLVGDSGVGKTCLLVRFKDGAFLAGTFISTVGIDFRNKVLDVDGMKVKLQIWDTAGQERF   60

Query:  304  RSVTHAYYRDAQALLLLYDITNQSSFDNIRAWLTEIHEYAQRDVVIMLLGNKADVSSERV  483
             RSVTHAYYRDA ALLLLYDITN+ SFDNI+ AWLTEI  EYAQ+DVV+MLLGNK D + ERV
Sbjct:  61   RSVTHAYYRDAHALLLLYDITNKDSFDNIQAWLTEIQEYAQQDVVLMLLGNKVDSTQERV  120

Query:  484  IRSEDGETLAREYGVPFMETSAKTGMNVELAFLAIAKELKYRAGRQPDEPSFQIRDYVES  663
             ++ EDGE LA+EYG +PFMETSAK+G+NV+LAF AIAKELK R+ + P EP F++ DYV+
Sbjct:  121  VKREDGEKLAKEYGLPFMETSAKSGLNVDLAFTAIAKELKQRSTKAPSEPRFRLHDYVKR  180

Query:  664  QKKRSSCCCSFV.Stop   687   TCCTTTGTGTGA
             + + SCC
Sbjct:  181  EGRGVSCCPL          188         S    F    V
```

FIG._7

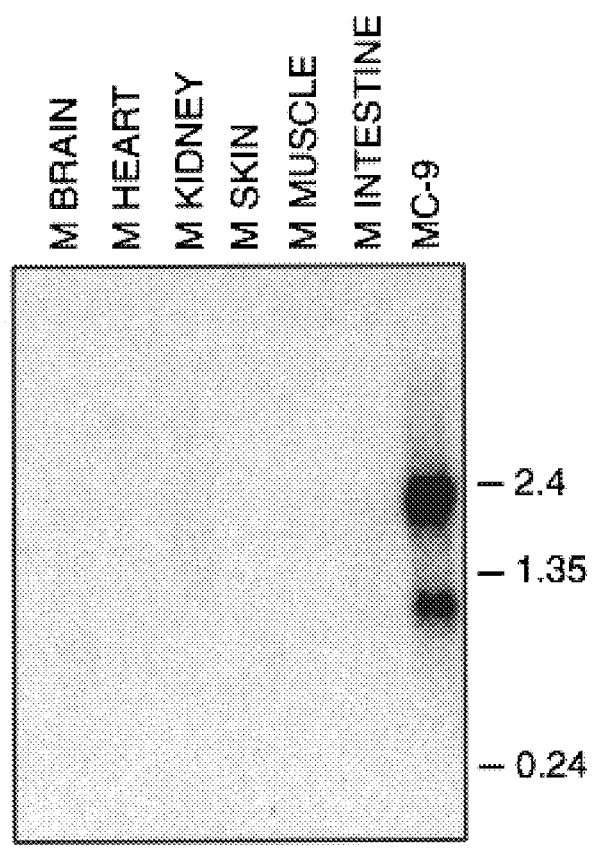
FIG._8

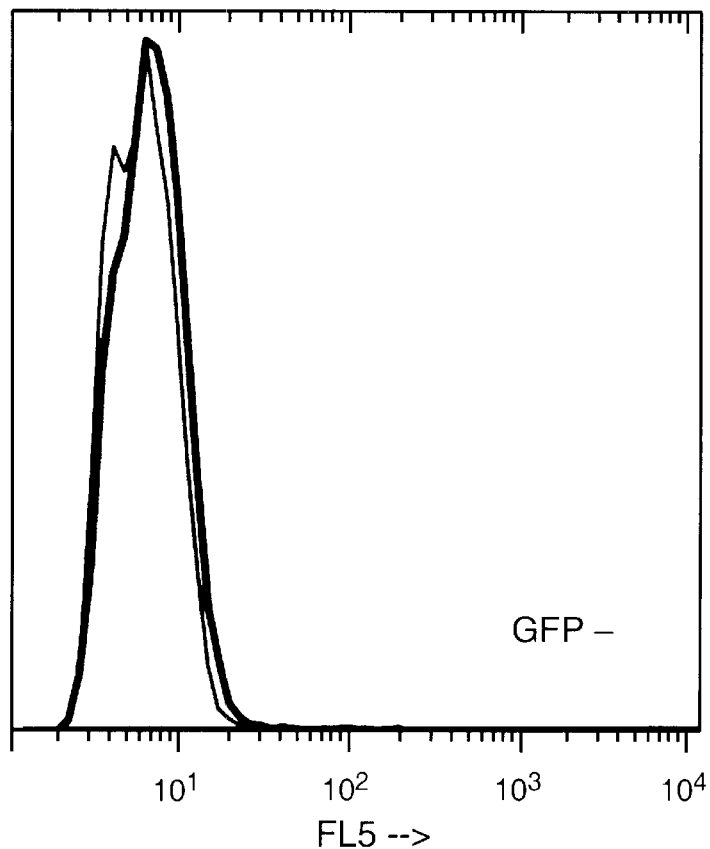
FIG._9A
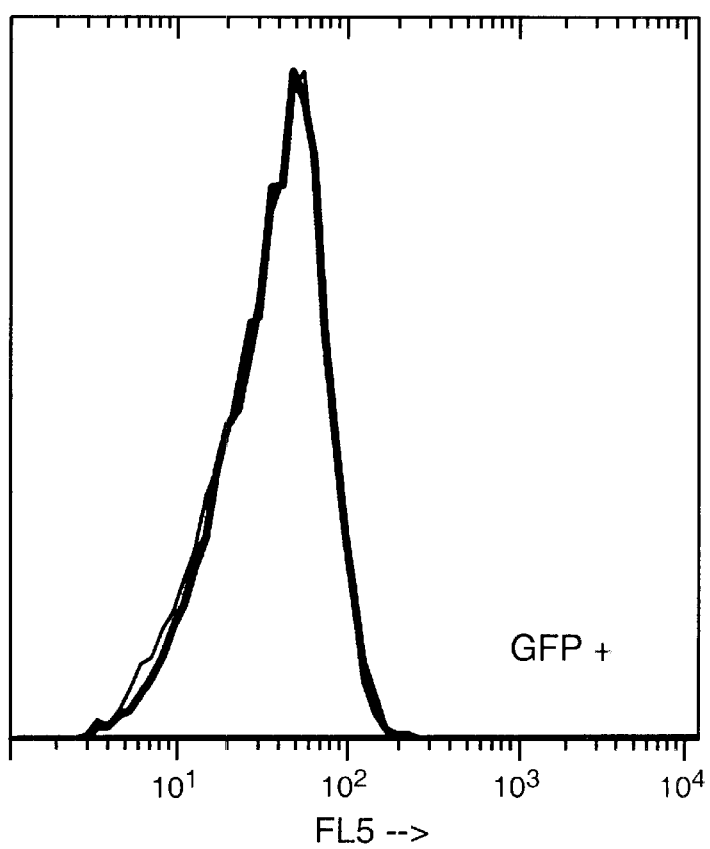
FIG._9B

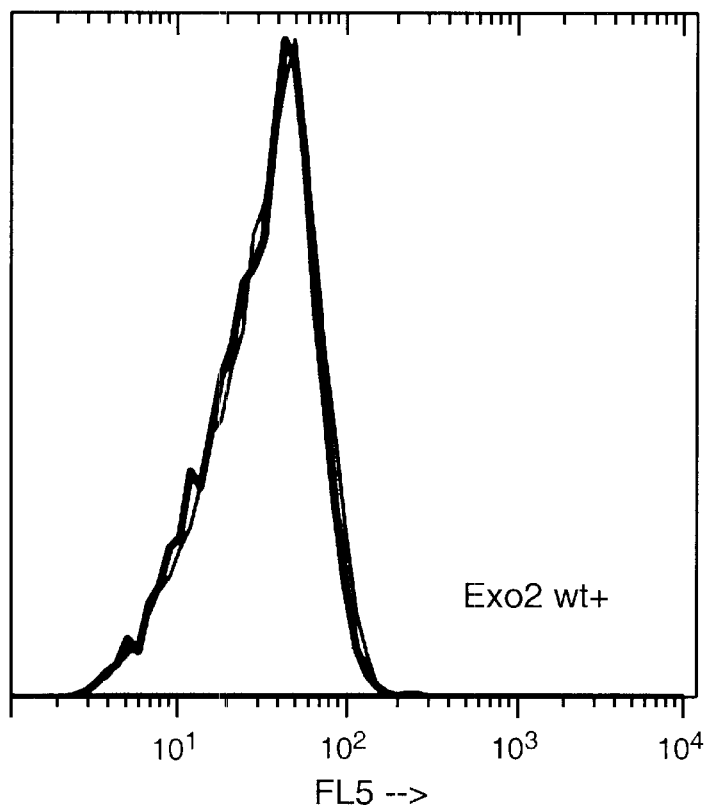
FIG._9C
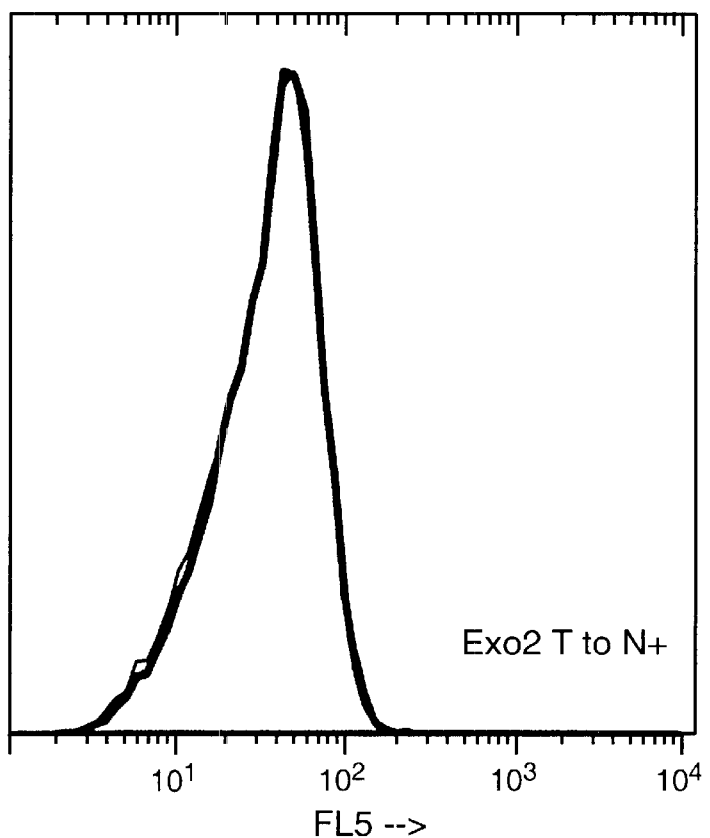
FIG._9D

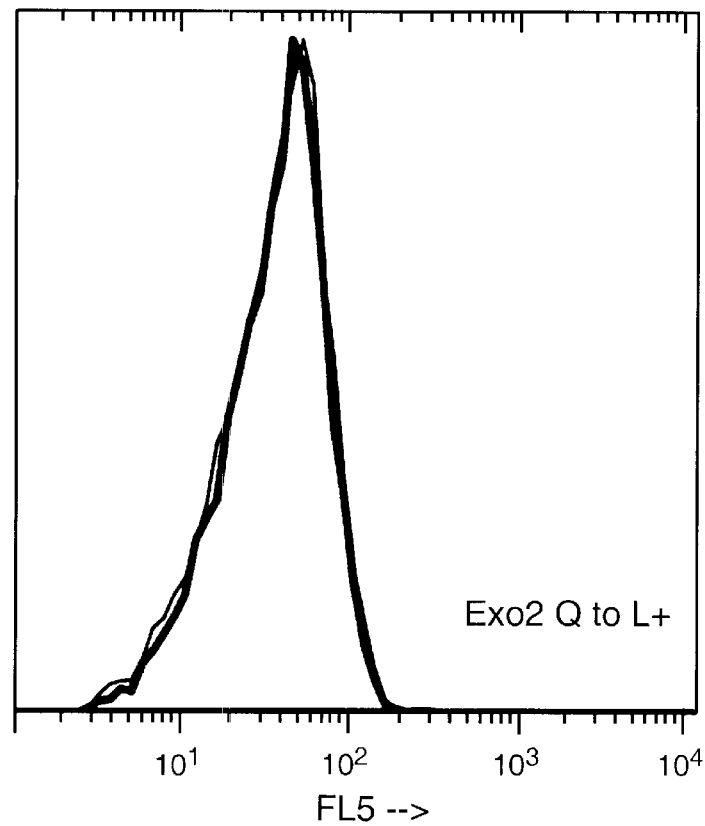
FIG._9E
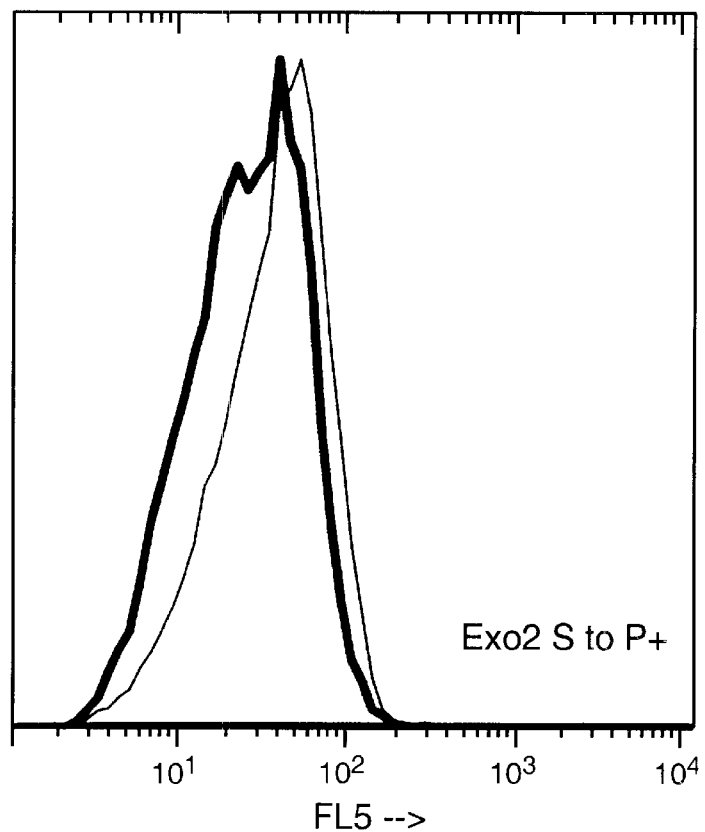
FIG._9F

```
Thursday, February 18, 1999 1:24 PM
Lipman-Pearson Protein Alignment
Ktuple: 2;  Gap Penalty: 4;  Gap Length Penalty: 12
Seq1(1>224)    Seq2(1>206)   Similarity   Gap    Gap   Consensus
muRab26h.pep   6-1. 1710002-muRab8   Index Number Length   Length
   (26>198)      (5>176)       54.6      1       1       173 v30       v40       v50       v60       v70       v80       v90      v100      v110
muRab26h.pep         FSPNYDLTGKVMLLGDSGVGKTCFLIQFKDGAFLSGTFIATVGIDFRNKVVTVDGARVKLQIWDTAGQERFRSVTHAYYRDAQALLLLYD
                     ...YD    K::L:GDSGVGKTC L::F:::AF ::TFI:T:GIDF: ...:DG R:KLQIWDTAGQERFR:: T AYYR:A :::L:YD
6-1. 1710002-muRab8  MAKTYDYLFKLLLIGDSGVGKTCVLFRFSEDAF-NSTFISTIGIDFKIRTIELDGKRIKLQIWDTAGQERFRTIITAYYRGAMGIMLVYD
                      ^10       ^20       ^30       ^40       ^50       ^60       ^70       ^80
                              v120      v130      v140      v150      v160      v170      v180      v190      v200
muRab26h.pep         ITNQSSFDNIRAWLTEIHEYAQRDVVIMLLGNKADVSSERVIRSEDGETLAREYGVPFMETSAKTGMNVELAFLAIAKELKYRAGRQPDE
                     ITN:..SFDNIR.W: ::I:.E.A  DV  M:LGNK DV...R :.. E GE.LA .YG: FMETSAK:..NVE AF:::A:::K ::::
6-1. 1710002-muRab8  ITNEKSFDNIRNWIRNIEEHASADVEKMILGNKCDVNDKRQVSKERGEKLALDYGIKFMETSAKANINVENAFFTLARDIKAKMDKNWKA
                       ^90      ^100      ^110      ^120      ^130      ^140      ^150      ^160      ^170
                              v210      v220
muRab26h.pep         PSFQIRDYVESQKKRSSCCSFV.
                     :.  V   :  ..  SF
6-1. 1710002-muRab8  TAAGSSHGVKITVEQQKRTSFFR
                       ^180      ^190      ^200
```

*FIG._10A*

Thursday, February 18, 1999 1:24 PM
Lipman-Pearson Protein Alignment
Ktuple: 2; Gap Penalty: 4; Gap Length Penalty: 12

| Seq1(1>224) | Seq2(1>220) | Similarity | Gap Index Number | Gap Length | Consensus Length |
|---|---|---|---|---|---|
| muRab26h.pep | human Rab-03A. | 46.6 | 1 | 1 | 160 |

```
                 v10       v20       v30       v40       v50       v60       v70       v80       v90       v100
muRab26h.pep  (25>184)  ATAGGDGEAPERSPPFSPNYDLTGKVMLLGDSGVGKTCFLIQFKDGAFLSGTFIATVGIDFRNKVVTVDGARVKLQIWDTAGQERFRSVTHAYYRDAQALL
                       :.:.       .N:.D  K:.:.:G::S:.VGKT.FL.:.: D::F .: .F::TVGIDF: K.: .: R: KLQIWDTAGQER: R::T AYYR: A ::: 
human Rab-03A. (18>176) MASATDSRYGQKESSDONFDYMFKILIIGNSSVGKTSFLFRYADDSF-TPAFVSTVGIDFKVKTIYRNDKRIKLQIWDTAGQERYRTITTAYYRGAMGFI
                             ^10       ^20       ^30       ^40       ^50       ^60       ^70       ^80       ^90 v110      v120      v130      v140      v150      v160      v170      v180      v190      v200
muRab26h.pep  LLYDITNQSSFDNIRAWLTEIHEYAQRDVIMLLGNKADVSSERVIRSEDGETLAREYGVPFMETSAKTGMNVELAFLAIAKELKYRAGRQPDEPSFQIR
              L:YDITN: SF.:.: W T:I.:Y: .::L:GNK D:.. ERV:.SE G LA.:. G F.E: SAK. .:NV. :F ... .:. D....:.
human Rab-03A. LMYDITNEESFNAVQDWSTQIKTYSWDNAQVLLVGNKCDMEDERVVSSERGRQLADHLGFEFFEASAKDNINVKQTFERLVDVICEKMSESLDTADPAVT
                     ^110      ^120      ^130      ^140      ^150      ^160      ^170      ^180      ^190 v210      v220
muRab26h.pep  DYVESQKKRSSCCSFV.
              :. :.: . .
human Rab-03A. GAKQGPQLSDQQVPPHQ
                     ^200      ^210
```

FIG._10B

EXO1 AND EXO2, EXOCYTOTIC PROTEINS

This is a continuation-in-part application of U.S. application Ser. No. 60/075,534, filed Feb. 23, 1998, pending, and a continuation-in-part application of U.S. application Ser. No. 60/086,650, filed May 26, 1998, pending.

FIELD OF THE INVENTION

The invention relates to novel Exo1 and Exo2 proteins, nucleic acids and antibodies. The invention further relates to the use of bioactive agents such as Exo1 and Exo2 proteins, nucleic acids and antibodies for the diagnosis and treatment of disease.

BACKGROUND OF THE INVENTION

Exocytosis is the fusion of secretory vesicles with the cellular plasma membrane, and has two main functions. One is the discharge of the vesicle contents into the extracellular space, and the second is the incorporation of new proteins and lipids into the plasma membrane itself.

Exocytosis can be divided into two classes: constitutive and regulated. All eukaryotic cells exhibit constitutive exocytosis, which is marked by the immediate fusion of the secretory vesicles after formation. Regulated exocytosis is restricted to certain cells, including exocrine, endocrine and neuronal cells. Regulated exocytosis results in the accumulation of the secretory vesicles that fuse with the plasma membrane only upon receipt of an appropriate signal, usually (but not always) an increase in the cytosolic free $Ca^{2+}$ concentration. Regulated exocytosis is crucial to many specialized cells, including neurons (neurotransmitter release), adrenal chromaffin cells (adrenaline secretion), pancreatic acinar cells (digestive enzyme secretion), pancreatic β-cells (insulin secretion), mast cells (histamine secretion), mammary cells (milk protein secretion), sperm (enzyme secretion), egg cells (creation of fertilization envelope) and adipocytes (insertion of glucose transporters into the plasma membrane). In addition, current theory suggests that the mechanisms of vesicle docking and fusion is conserved from yeast to mammalian brain.

Some insights into the process of regulated secretion at the molecular level have allowed the definition of G proteins as important regulators. Early experiments showed that non-hydrolyzable analogues of GTP could induce secretion in peritoneal mast cells (Fernandez et al., Nature 312:453 (1984)). More recently, a large body of evidence has been accumulating implicating small G proteins of the rab family as regulators in the fusion of secretory granules with plasma membranes during exocytosis. The rab proteins are a branch of the Ras superfamily of small GTPases. To date, the yeast rab family has 11 proteins, while over 40 ras-related proteins have been found in mammalian cells. The rab GTPases represent a diverse family of homologous proteins that are generally associated with the membrane of organelles in a wide variety of cells, where they regulate defined steps of intracellular membrane traffic (Zerial et al., Curr. Opin. Cell. Biol. 5:613 (1993)). An example of this are the rab3 subfamily proteins which have been found to have limited expression in regulated secretion-competent cells, and to be associated with synaptic or secretory granules, suggesting that they are involved in stimulus-secretion coupling (Lledo et al., Trends. Neurobiol. Sci. 17:426 (1994)). Further, overexpression of rab3D or its GTP binding mutant form (N135I) in the rat basophil line RBL leads to significant inhibition of IgE mediated exocytosis (Roa et al., J. Immunol. 159:2815 (1997)). Thus it appears that tissue/cell specific isoforms of rab proteins may play particular roles in regulated secretory responses.

In addition, disorders involving exocytosis are known. For example, inflammatory mediator release from mast cells leads to a variety of disorders, including asthma. Similarly, Chediak-Higashi Syndrome (CHS) is a rare autosomal recessive disease in which neutrophils, monocytes and lymphocytes contain giant cytoplasmic granules. Similar disorders have been described in mice, mink, cattle, cats, and killer whales, with the murine homolog of CHS (designated beige or bg) being the best characterized. See Perou et al., J. Biol. Chem. 272(47):29790 (1997) and Barbosa et al., Nature 382:262 (1996), both of which are hereby incorporated by reference.

Accordingly, the proteins involved in exocytosis are of paramount interest, and it is an object of the invention to provide Exo1 and Exo2 proteins and related molecules. It is a further object of the invention to provide recombinant nucleic acids encoding Exo1 and Exo2 proteins, and expression vectors and host cells containing the nucleic acid encoding the Exo1 and Exo2 proteins. A further object of the invention is to provide methods for screening for antagonists and agonists of Exo1 and Exo2.

BRIEF DESCRIPTION OF THE DRAWINGS

FIG. 1 depicts the Exo1 nucleotide (SEQ ID NO:1) and amino acid (SEQ ID NO:2) sequences. The underlined region is the region of homology to the Chediak Higashi Syndrome protein.

FIGS. 2A, 2B, 2C and 2D depict the cDNA screening for inhibitors of mast cell exocytosis using fluorescent-activated cell sorting (FACS). cDNA from MC-9, a murine mast cell line put into a retroviral vector system as known in the art. FIG. 2A shows two overlaid graphs; the one on the left is unstimulated cells; the one on the right is stimulated with ionomycin, which stimulates exocytosis in mast cells. Both cell populations were treated with annexin-PerCP, a fluorescent dye that binds to the secretory granules on the surface; if exocytosis is occuring, annexin binds, leading to an increase in fluorescence. A population of cells from the stimulated cells that did not appear to increase in fluorescence were picked and allowed to grow for a period of time and then resorted, shown in FIG. 2B. FIG. 2B shows a "shoulder" developing on the stimulated cells, comprising cells that do not bind annexin in the presence of ionomycin. This population was allowed to grow and resorted again, shown in FIG. 2C, and the non-stimulating cells grown and resorted a final time, in FIG. 2D. FIG. 3 shows that the B2.6 clone (also termed "Exo1" herein) inhibits mast cell exocytosis, as shown in mast cells stimulated with ionomycin and treated with annexin. The cells containing the Exo1 clone do not significantly bind annexin, thus showing that exocytosis is inhibited.

FIGS. 4A and 4B shows that the Exo1 protein is homologous to the Chediak Higashi Syndrome protein (CHp). FIG. 4A shows the primary sequence homology between a region of Exo1 protein (B2.6: SEQ ID NO:3) and a region of CHp (SEQ ID NO:4). FIG. 4B shows the secondary structure prediction homology.

FIG. 5 depicts the structural similarities between the Chediak-Higashi Syndrome protein and Exo1. (SEQ ID NO:9 and SEQ ID NO:10 [left and right, respectively])

FIG. 6 depicts the nucleotide sequence of mouse Exo2 (SEQ ID NO:6). The start codon is underlined.

FIG. 7 depicts the amino acid sequence of mouse Exo2 (SEQ ID NO:7) and the comparison to the rat Rab26 protein (SEQ ID NO:5). The Exo2 and Rab26 consensus sequence is shown (SEQ ID NO:8).

FIG. 8 shows a northern blot showing the expression of Exo2 in different mouse tissues. Lane 1, mouse brain; lane 2; heart; lane 3, kidney; lane 4, skin; lane 5, muscle; lane 6, intestine; lane 7, mast cell. The Exo2 expression is highly specific to mast cells.

FIG. 9A–F shows the expression of an Exo2 mutant can inhibit exocytosis in primary mouse bone marrow derived mast cells (BMMC). Primary bone marrow derived mast cells were infected with recombinant retroviruses expresing either the wild type (wt) green fluorescent protein (GFP) (FIGS. 9A and 9B), or fusion proteins of Exo2 and GFP (FIGS. 9D, 9E, and 9F). FIG. 9A shows BMMCs infected with GFPwt virus; a FACS plot looking at Annexin-V fluorescence using GFP gating. The shaded area represent uninfected cells and the leavy line represents GFPwt virus infected cells. Note the overlap of the two populations. FIG. 9B shows the same cells as in FIG. 9A but stimulated with 2 micromolar ionomycin. The annexin signal is greatly increased indicative of the exocytic process and the GFP$^-$ and GFP$^+$ cells behave identically. FIG. 9C shows BMMC infected with the Exo2 wild type fused to GFP and ionomycin stimulated. There is no inhibitory effect seen with this construct. FIG. 9D shows BMMC infected with the Exo2 T to N mutant (position 43) fused to GFP and ionomycin stimulated. There is no inhibitory effect seen with the construct.

FIG. 9E shows BMMC infected with the Exo2 Q to L mutant (position 89) fused to GFP and ionomycin stimulated. There is no inhibitory effect seen with the construct. FIG. 9F shows BMMC infected with the Exo2 S to P mutant (position 212) fused to GFP and ionomycin stimulated. A significant inhibitory effect is seen in the GFP$^+$ population indicative that this Exo2 mutant can effect exocytosis in the primary mast cells.

FIG. 10A shows an alignment of Exo2 (muRab26h.pep) (SEQ ID NO:11) with mouse rab8 (muRab8) (SEQ ID NO:12) with a consensus sequence(SEQ ID NO:13) shown between Exo2 and rab8. Exo2 and mouse rab8 are 49% identical. FIG. 10B shows an alignment of Exo2 (muRab26h.pep)(SEQ ID NO:14) with-human Rab-03A (SEQ ID NO:15) with a consensus sequence(SEQ ID NO:16) shown between. Exo2 and human Rab-03A are 35% identical. Key: ":"=strongly conserved; "."=weakly conserved.

DETAILED DESCRIPTION OF THE INVENTION

The present invention provides novel exocytotic proteins and nucleic acids. In a preferred embodiment, the exocytotic proteins are from vertebrates and more preferably from mammals, including rodents (rats, mice, hamsters, guinea pigs, etc.), primates, farm animals (including sheep, goats, pigs, cows, horses, etc) and in the most preferred embodiment, from humans. However, using the techniques outlined below, exocytotic proteins from other organisms may also be obtained.

By "exocytotic protein" is meant an Exo1 or an Exo2 protein. An Exo1 and Exo2 protein of the present invention may be identified in several ways. "Protein" in this sense includes proteins, polypeptides, and peptides. An Exo1 and Exo2 nucleic acid or Exo1 and Exo2 protein is initially identified by substantial nucleic acid and/or amino acid sequence homology to the sequences shown in FIGS. 1, 6 and/or 7. Such homology can be based upon the overall nucleic acid or amino acid sequence.

As used herein, a protein is a "Exo1 protein" if the overall homology of the protein sequence to the amino acid sequences shown in FIG. 1 is preferably greater than about 50%, more preferably greater than about 60%, even more preferably greater than about 75% and most preferably greater than 80. In some embodiments the homology will be as high as about 90 to 95 or 98%.

As used herein, a protein is a "Exo2 protein" if the overall homology of the protein sequence to the amino acid sequences shown in FIG. 7 is preferably greater than about 75%, more preferably greater than about 80%, even more preferably greater than about 85% and most preferably greater than 90%. In some embodiments the homology will be as high as about 93 to 95 or 98%.

Homology in this context means sequence similarity or identity, with identity being preferred. This homology will be determined using standard techniques known in the art, such as the Best Fit sequence program described by Devereux et al., *Nucl. Acid Res.* 12:387–395 (1984), preferably using the default settings, or the BLASTX program (Altschul et al., J. Mol. Biol. 215, 403–410). The alignment may include the introduction of gaps in the sequences to be aligned. In addition, for sequences which contain either more or fewer amino acids than the protein shown in FIGS. 1 and 7, it is understood that the percentage of homology will be determined based on the number of homologous amino acids in relation to the total number of amino acids. Thus, for example, homology of sequences shorter than that shown in the Figures, as discussed below, will be determined using the number of amino acids in the shorter sequence.

Similarity is determined using standard techniques known in the art, including, but not limited to, the algorithm of Smith & Waterman, Adv. Appl. Math. 2:482 (1981), by the algorithm of Needleman & Wunsch. J. Mol. Biol. 1970. 48:443, by the search for similarity method of Pearson & Lipman. 1988. PNAS USA 85:2444, by computerized implementations of these algorithms (GAP, BESTFIT, FASTA, and TFASTA in the Wisconsin Genetics Software Package, Genetics Computer Group, 575 Science Drive, Madison, Wis.), or the Best Fit sequence program described by Devereux et al. *Nucl. Acid Res.* 1984. 12:387–395.

In a preferred embodiment, percent identity or similarity is calculated by FastDB based upon the following parameters: mismatch penalty of 1.0; gap penalty of 1.0; gap size penalty of 0.33, joining penalty of 30.0. ("Current Methods in Comparison and Analysis", Macromolecule Sequencing and Synthesis, Selected Methods and Applications, pp. 127–149, 1998. Alan R. Liss, Inc.)

Another example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng and Doolittle. J. Mol. Evol. 1987. 35:351–360; the method is similar to that described by Higgins and Sharp. 1989. CABIOS 5:151–153. Useful PILEUP parameters including a default gap weight of 3.00, a default gap length weight of 0.10, and weighted end gaps.

An additional example of a useful algorithm is the BLAST algorithm, described in Altschul et al. J. Mol. Biol. 1990. 215:403–410 and Karlin et al., PNAS USA 1993. 90:5873–5787. A particularly useful BLAST program is the WU-BLAST-2 program which was obtained from Altschul et al., Methods in Enzymology. 1996. 266: 460–480.

WU-BLAST-2 uses several search parameters, most of which are set to the default values. The adjustable parameters are set with the following values: overlap span =1, overlap fraction =0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

In an alternative embodiment, percent amino acid sequence identity is determined. In percent identity calculations relative weight is not assigned to various manifestations of sequence variation, such as, insertions, deletions, substitutions, etc. Only identities are scored positively (+1) and all forms of sequence variation given a value of "0", which obviates the need for a weighted scale or parameters as described above for sequence similarity calculations. Therefore, percent identity represents a highly rigorous method of comparing sequences.

Percent sequence identity can be calculated, for example, by dividing the number of matching identical residues by the total number of residues of the "shorter" sequence in the aligned region and multiplying by 100. The "longer" sequence is the one having the most actual residues in the aligned region.

Exocytotic proteins of the present invention may be shorter or longer than the amino acid sequences shown in the Figures. Thus, in a preferred embodiment, included within the definition of exocytotic proteins are portions or fragments of the sequences depicted in the Figures. For example, Exo1 and Exo2 deletion mutants can be made. Thus, in a preferred embodiment, the Exo1 and Exo2 proteins of the present invention are, respectively, Exo1 and Exo2 polypeptides.

In a preferred embodiment, the exocytotic proteins are derivative or variant Exo1 and Exo2 proteins. That is, as outlined more fully below, the derivative Exo1 and Exo2 peptides will contain at least one amino acid substitution, deletion or insertion, with amino acid substitutions being particularly preferred. The amino acid substitution, insertion or deletion may occur at any residue within the Exo1 and Exo2 peptide.

In addition, as is more fully outlined below, exocytotic proteins can be made that are longer than those depicted in the figures, for example, by the addition of epitope or purification tags, the addition of other fusion sequences, etc.

Exocytotic proteins may also be identified as being encoded by exocytotic nucleic acids. Thus, Exo1 proteins are encoded by nucleic acids that will hybridize to the sequence depicted in FIG. 1 or its complement and Exo2 proteins are encoded by nucleic acids that will hybridize to the sequence depicted in FIG. 6, or its complement, as outlined herein.

In a preferred embodiment, when the Exo1 and Exo2 proteins are to be used to generate antibodies, the Exo1 and Exo2 proteins must share at least one epitope or determinant with their respective full length proteins shown in FIGS. 1 and 6. By "epitope" or "determinant" herein is meant a portion of a protein which will generate and/or bind an antibody. Thus, in most instances, antibodies made to a smaller exocytotic protein will be able to bind to the full length protein. In a preferred embodiment, the epitope is unique; that is, antibodies generated to a unique epitope show little or no cross-reactivity.

In a preferred embodiment, the antibodies to Exo1 or Exo2 are capable of reducing or eliminating the biological function of Exo1 or Exo2, as is described below. For example, the addition of anti-Exo1 antibodies (either polyclonal or preferably monoclonal) to Exo1 (or cells containing Exo1 ) also may reduce or eliminate the Exo1 activity. In a preferred embodiment , anti-Exo2 antibodies (either polyclonal or preferably monoclonal) to Exo2 (or cells containing Exo2) may reduce or eliminate the Exo2 activity. Generally, at least a 25% decrease in activity is preferred, with at least about 50% being particularly preferred and about a 95–100% decrease being especially preferred.

Antibodies of the invention specifically bind to either Exo1 or Exo2 proteins. By "specifically bind" herein is meant that the antibodies bind to the protein with a binding constant in the range of at least $10^{-4}$–$10^{-6}$ $M^{-1}$, with a preferred range being $10^{-7}$–$10^{-9}$ $M^{-1}$.

In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence. Thus the homology of the nucleic acid sequence as compared to the nucleic acid sequence of either FIG. 1 or FIG. 6 is preferably greater than 75%, more preferably greater than about 80%, particularly greater than about 85% and most preferably greater than 90%. In some embodiments the homology will be as high as about 93 to 95 or 98%.

Nucleic acid similarity can be determined using, for example, BLASTN (Altschul et al. 1990. J. Mol. Biol. 147:195–197). BLASTN uses a simple scoring system in which matches count +5 and mismatches –4. To achieve computational efficiency, the default parameters have been incorporated directly into the source code.

In a preferred embodiment, Exo1 or Exo2 nucleic acids encode, respectively, an Exo1 or Exo2 protein. As will be appreciated by those in the art, due to the degeneracy of the genetic code, an extremely large number of nucleic acids may be made, all of which encode the Exo1 or Exo2 proteins of the present invention. Thus, having identified a particular amino acid sequence, those skilled in the art could make any number of different nucleic acids, by simply modifying the sequence of one or more codons in a way which does not change the amino acid sequence of the encoded exocytotic.

In one embodiment, the nucleic acid homology is determined through hybridization studies. Thus, for example, nucleic acids which hybridize under high stringency to the nucleic acid sequences shown in FIGS. 1 or 6 or their complements are considered an exocytotic gene.

High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference.

High stringency conditions are known in the art; see for example Maniatis et al., Molecular Cloning: A Laboratory Manual, 2d Edition, 1989, and Short Protocols in Molecular Biology, ed. Ausubel, et al., and, Hames and Higgins, eds. *Nucleic Acid Hybridization, A Practical Approach*, IL press, Washington, D.C., 1985; Berger and Kimmel eds. *Methods in Enzymology, Vol. 52, Guide to Molecular Cloning Techniques*, Academic press Inc., New York, N.Y., 1987; and Bothwell, Yancopoulos and Alt, eds, *Methods for Cloning and Analysis of Eukaryotic Gene*, Jones and Bartlett Publishers, Boston, Mass. 1990, which are hereby expressly incorporated by reference in their entirety.

The choice of hybridization conditions will be evident to one skilled in the art and will generally be guided by the purpose of the hybridization, the type of hybridization (DNA-DNA, DNA-RNA, RNA-RNA, oligonucleotide-DNA etc.), and the level of desired relatedness between the sequences. Methods for hybridization are well established in the literature. For example, one or ordinary skill in the art realizes that the stability of nucleic acid duplexes will decrease with an increased number and proximity of mismatched bases; thus, the stringency of hybridization may be used to maximize or minimize the stability of such duplexes. Hybridiziation stringency can be altered by, for example, adjusting the temperature of hybridization solution; adjusting the percentage of helix-destabilizing agents, such as, formamide, in the hybridization solution; and adjusting the temperature and salt concentration of the wash solutions. In general, the stringency of hybridization is adjusted during the post-hybzidization washes by varying the salt concentration and/or the temperature. Stringency of hybridization may be increased, for example, by: i) increasing the percentage of formamide in the hybridization solution; ii) increasing the temperature of the wash solution; or iii) decreasing the ionic strength of the wash solution. High stringency conditions may involve high temperature hybridization (e.g. 65° C.–68° C. in aqueous solution containing 4–6×SSC, or 42° C. in 50% formamide) combined with high temperature (e.g., 5° C.–25° C. below the $T_m$) and a low salt concentration (e.g., 0.1×SSC) washes. Reduced stringency conditions may involve lower hybridization temperatures (e.g., 35° C.–42° C. in 20–50% formamide) with intermediate temperature (e.g., 40° C.–60° C.) washes in a higher salt concentration (e.g., 2–6×SSC). Moderate stringency conditions, which may involve hybridization at a temperature between 50° C.–55° C. and washes in 0.1×SSC, 0.1% SDS at between 50° C. and 55° C., may be used (see Maniatis and Ausubel, supra). In a preferred embodiment, nucleic acids which hybridize to the nucleic acids herein have the biological activity as described herein.

The exocytotic proteins and nucleic acids of the present invention are preferably recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick"); thus the sequence depicted in FIGS. 1 and 6 also includes the complement of the sequences. By the term "recombinant nucleic acid" herein is meant nucleic acid, originally formed in vitro, in general, by the manipulation of nucleic acid by endonucleases, in a form not normally found in nature. Thus an isolated Exo1 or Exo2 nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of an Exo2 protein from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag or amino acid substitutions, insertions and deletions, as discussed below.

Also included within the definition of exocytotic proteins of the present invention are amino acid sequence variants. These variants fall into one or more of three classes: substitutional, insertional or deletional variants. These variants ordinarily are prepared by site specific mutagenesis of nucleotides in the DNA encoding the Exo1 or Exo2 protein, using cassette or PCR mutagenesis or other techniques well known in the art, to produce DNA encoding the variant, and thereafter expressing the DNA in recombinant cell culture as outlined above. However, variant Exo1 or Exo2 protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the Exo1 and Exo2 protein amino acid sequences. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed Exo1 or Exo2 variants screened for the optimal combination of desired activity. Techniques for making substitution mutations at predetermined sites in DNA having a known sequence are well known, for example, M13 primer mutagenesis and PCR mutagenesis. Screening of the mutants is done using assays of Exo1 or Exo2 protein activities; for example, inhibition of exocytosis assays may be done. Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the Exo1 or Exo2 protein are desired, substitutions are generally made in accordance with the following chart:

Chart 1

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

In an alternative embodiment, a library of variants are generated by an entirely, non-specific, random mutagenesis method. These techniques are known in the art and do not require the selection of a specific cite or region to be altered. For example, DNA shuffling as described by Stemmer. *Nature* 370:389–391 (1994) and Stemmer. *PNAS USA* 91:10747–10751 (1994)) can be used to produce variants which are cloned, expressed, and screened for a desired property. For example, the intracellular activity of an exocytoic protein can be increased or decreased.

The variants typically exhibit the same qualitative biological activity and will elicit the same immune response as the naturally-occurring analogue, although variants also are selected to modify the characteristics of the Exo1 or Exo2 protein as needed. Alternatively, the variant may be designed such that the biological activity of the Exo1 or Exo2 protein is altered. For example, glycosylation sites may be altered or removed.

Covalent modifications of Exo1 and Exo2 polypeptides are included within the scope of this invention. One type of covalent modification includes reacting targeted amino acid residues of an Exo1 or Exo2 polypeptide with an organic derivatizing agent that is capable of reacting with selected side chains or the N-or C-terminal residues of an Exo1 or Exo2 polypeptide. Derivatization with bifunctional agents is useful, for instance, for crosslinking Exo1 or Exo2 to a water-insoluble support matrix or surface for use in the method for purifying anti-Exo1 or anti-Exo2 antibodies, respectively, or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis-(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the amino groups of lysine, arginine, and histidine side chains [T. E. Creighton, *Proteins: Structure and Molecular Properties*, W. H. Freeman & Co., San Francisco, pp. 79–86 (1983)], acetylation of the N-terminal amine, and amidation of any C-terminal carboxyl group.

Another type of covalent modification of the exocytotic proteins included within the scope of this invention comprises altering the native glycosylation pattern of the polypeptide. "Altering the native glycosylation pattern" is intended for purposes herein to mean deleting one or more carbohydrate moieties found in native sequence Exo1 or Exo2 polypeptide, and/or adding one or more glycosylation sites that are not present in the native sequence Exo1 or Exo2 polypeptide.

Addition of glycosylation sites to Exo1 or Exo2 polypeptides may be accomplished by altering the amino acid sequence thereof. The alteration may be made, for example, by the addition of, or substitution by, one or more serine or threonine residues to the native sequence Exo1 or Exo2 polypeptide (for O-linked glycosylation sites). The Exo1 or Exo2 amino acid sequence may optionally be altered through changes at the DNA level, particularly by mutating the DNA encoding the Exo1 or Exo2 polypeptide at preselected bases such that codons are generated that will translate into the desired amino acids.

Another means of increasing the number of carbohydrate moieties on the exocytotic proteins is by chemical or enzymatic coupling of glycosides to the polypeptide. Such methods are described in the art, e.g., in WO 87/05330 published Sep. 11, 1987, and in Aplin and Wriston, *CRC Crit. Rev. Biochem*., pp. 259–306 (1981).

Removal of carbohydrate moieties present on the Exo1 or Exo2 polypeptides may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys*., 259:52 (1987) and by Edge et al., *Anal. Biochem*., 118:131 (1981). Enzymatic cleavage of carbohydrate moieties on polypeptides can be achieved by the use of a variety of endo-and exo-glycosidases as described by Thotakura et al., *Meth. Enzymol*., 138:350 (1987).

Another type of covalent modification of Exo1 or Exo2 comprises linking the polypeptides to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

The exocytotic proteins of the present invention may also be modified in a way to form chimeric molecules comprising an Exo1 or Exo2 polypeptide fused to another, heterologous polypeptide or amino acid sequence. In one embodiment, such a chimeric molecule comprises a fusion of an Exo1 or an Exo2 polypeptide with a tag polypeptide which provides an epitope to which an anti-tag antibody can selectively bind. The epitope tag is generally placed at the amino-or carboxyl-terminus of Exo1 or Exo2 polypeptide. The presence of such epitope-tagged forms of an Exo1 or Exo2 polypeptide can be detected using an antibody against the tag polypeptide. Also, provision of the epitope tag enables the Exo1 and Exo2 polypeptide to be readily purified by affinity purification using an anti-tag antibody or another type of affinity matrix that binds to the epitope tag. In an alternative embodiment, the chimeric molecule may comprise a fusion of an Exo1 or Exo2 polypeptide with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159–2165 (1988)]; the c-myc tag and the 8F9, 3C7, 6E10, G4, B7 and 9E10 antibodies thereto [Evan et al., *Molecular and Cellular Biology*, 5:3610–3616 (1985)]; and the Herpes Simplex virus glycoprotein D (gD) tag and its antibody [Paborsky et al., *Protein Engineering*, 3(6):547–553 (1990)]. Other tag polypeptides include the Flag-peptide [Hopp et al., BioTechnology, 6:1204–1210 (1988)]; the KT3 epitope peptide [Martin et al., *Science*, 255:192–194 (1992)]; tubulin epitope peptide [Skinner et al., *J. Biol. Chem.*, 266:15163–15166 (1991)]; and the T7 gene 10 protein peptide tag [Lutz-Freyermuth et al., *Proc. Natl. Acad. Sci. USA*, 87:6393–6397 (1990)].

Also included with the definition of exocytotic proteins are other Exo1 and Exo2 proteins of the, respective, Exo1 and Exo2 families, and Exo1 and Exo2 proteins from other organisms, which are cloned and expressed as outlined below. Thus, probe or degenerate polymerase chain reaction (PCR) primer sequences may be used to find other related Exo1 and Exo2 proteins from humans or other organisms. As will be appreciated by those in the art, particularly useful probe and/or PCR primer sequences include the unique areas of the Exo1 and Exo2 nucleic acid sequences. As is generally known in the art, preferred PCR primers are from about 15 to about 35 nucleotides in length, with from about 20 to about 30 being preferred, and may contain inosine as needed. The conditions for the PCR reaction are well known in the art.

Once the Exo1 or Exo2 nucleic acid is identified, it can be cloned and, if necessary, its constituent parts recombined to form the entire Exo1 or Exo2 nucleic acid. Once isolated from its natural source, e.g., contained within a plasmid or other vector or excised therefrom as a linear nucleic acid segment, the recombinant Exo1 or Exo2 nucleic acid can be further-used as a probe to identify and isolate other Exo1 or Exo2 nucleic acids. It can also be used as a "precursor" nucleic acid to make modified or variant Exo1 or Exo2 nucleic acids and proteins.

Using the nucleic acids of the present invention which encode an exocytotic protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the Exo1 or Exo2 protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the Exo1 or Exo2 protein; for example, transcriptional and translational regulatory nucleic acid sequences from Bacillus are preferably used to express the Exo1 or Exo2 protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

A preferred expression vector system is a retroviral vector system such as is generally described in PCT/US97/01019 and PCT/US97/01048, both of which are hereby expressly incorporated by reference.

The exocytotic proteins of the present invention are produced by culturing a host cell transformed with an expression vector containing nucleic acid encoding an Exo1 or Exo2 protein, under the appropriate conditions to induce or cause expression of the encoded protein. The conditions appropriate for Exo1 or Exo2 protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli, Bacillus subtilis*, SF9 cells, C129 cells, 293 cells, Neurospora, BHK, CHO, COS, and HeLa cells, fibroblasts, Schwanoma cell lines, immortalized mammalian myeloid and lymphoid cell lines, Jurkat cells, mast cells and other endocrine and exocrine cells, and neuronal cells.

In a preferred embodiment, the Exo1 or Exo2 proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for the Exo1 or Exo2 protein into mRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, Exo1 or Exo2 proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of Exo1 or Exo2 protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the Exo1 or Exo2 protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris*, and *Streptococcus lividans*, among others.

The bacterial expression vectors are transformed into bacterial host cells using techniques well known in the art, such as calcium chloride treatment, electroporation, and others.

In one embodiment, Exo1 or Exo2 protein is produced in insect cells. Expression vectors for the transformation of insect cells, and in particular, baculovirus-based expression vectors, are well known in the art.

In a preferred embodiment, Exo1 or Exo2 protein is produced in yeast cells. Yeast expression systems are well known in the art, and include expression vectors for *Saccharomyces cerevisiae, Candida albicans* and *C. maltosa, Hansenulapolymorpha, Kluyveromyces fragilis* and *K lactis*,

*Pichia guillerimondii* and *P. pastoris, Schizosaccharomyces pombe,* and *Yarrowia lipolytica*. Preferred promoter sequences for expression in yeast include the inducible GAL1, 10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

The exocytotic protein may also be made as a fusion protein, using techniques well known in the art. Thus, for example, for the creation of monoclonal antibodies, if the desired epitope is small, the Exo1 or Exo2 protein may be fused to a carrier protein to form an immunogen. Alternatively, the Exo1 or Exo2 protein may be made as a fusion protein to increase expression, or for other reasons. For example, when the Exo1 or Exo2 protein is a peptide, the nucleic acid encoding the peptide may be linked to other nucleic acid for expression purposes.

In one embodiment, the exocytotic nucleic acids, proteins and antibodies of the invention are labeled. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

In a preferred embodiment, the exocytotic protein is purified or isolated after expression. Exocytotic proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the Exo1 or Exo2 protein may be purified using a standard affinity column using antibody specific for Exo1 or Exo2. Ultrafiltration and diafiltration techniques, in conjunction with protein concentration, are also useful. For general guidance in suitable purification techniques, see Scopes, R., Protein Purification, Springer-Verlag, N.Y. (1982). The degree of purification necessary will vary depending on the use of the Exo2 protein. In some instances no purification will be necessary.

Once expressed and purified if necessary, the Exo1 and Exo2 proteins and nucleic acids are useful in a number of applications.

In a preferred embodiment, the Exo1 or Exo2 proteins, nucleic acids, modified proteins and cells containing the native or modified Exo1 or Exo2 proteins are used in screening assays. Identification of this important exocytotic protein permits the design of drug screening assays for compounds that modulate Exo1 or Exo2 activity.

Screens may be designed to first find candidate agents that can bind to exocytotic proteins, and then these agents may be used in assays that evaluate the ability of the candidate agent to modulate exocytotic activity. Thus, as will be appreciated by those in the art, there are a number of different assays which may be run; binding assays and activity assays.

Thus, in a preferred embodiment, the methods comprise combining an Exo1 or Exo2 protein and a candidate bioactive agent, and determining the binding of the candidate agent to the Exo1 or Exo2 protein. Preferred embodiments utilize the mouse or human Exo1 or Exo2 protein, although other mammalian proteins may also be used, including rodents (rats, hamsters, guinea pigs, etc.), farm animals (cows, sheep, pigs, horses, etc.) and primates. These latter embodiments may be preferred in the development of animal models of human disease. In some embodiments, as outlined herein, variant or derivative Exo1 or Exo2 proteins may be used, including deletion Exo1 or Exo2 proteins as outlined above.

Furthermore, included within the definition of exocytotic proteins are portions of Exo1 or Exo2 proteins; that is, either the full-length protein may be used, or functional portions thereof. In addition, the assays described herein may utilize either isolated Exo1 or Exo2 proteins or cells comprising the Exo1 or Exo2 protein.

Generally, in a preferred embodiment of the methods herein, the Exo1 or Exo2 protein or the candidate agent is non-diffusably bound to an insoluble support having isolated sample receiving areas (e.g. a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, Teflon™, etc. Microtiter plates and arrays are especially convenient because a large number of assays can be carried out simultaneously, using small amounts of reagents and samples. The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety.

A candidate bioactive agent is added to the assay. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The term "candidate bioactive agent" or "exogeneous compound" as used herein describes any molecule, e.g., protein, oligopeptide, small organic molecule, polysaccharide, polynucleotide, etc., with the capability of directly or indirectly altering the bioactivity of Exo1 or Exo2. Generally a plurality of assay mixtures are run in parallel with different agent concentrations to obtain a differential response to the various concentrations. Typically, one of these concentrations serves as a negative control, i.e., at zero concentration or below the level of detection.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In a preferred embodiment, the candidate bioactive agents are naturally occuring proteins or fragments of naturally occuring proteins. Thus, for example, cellular extracts containing proteins, or random or directed digests of proteinaceous cellular extracts, may be used. In this way libraries of procaryotic and eucaryotic proteins may be made for screening against Exo1 and Exo2. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occuring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169–176). Several nucleic acid analogs are described in Rawls, C & E News Jun. 2, 1997 page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occuring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As described above generally for proteins, nucleic acid candidate bioactive agents may be naturally occuring nucleic acids, random nucleic acids, or "biased" random nucleic acids. For example, digests of procaryotic or eucaryotic genomes may be used as is outlined above for proteins.

In a preferred embodiment, the candidate bioactive agents are organic chemical moieties, a wide variety of which are available in the literature.

The determination of the binding of the candidate bioactive agent to the Exo1 or Exo2 protein may be done in a number of ways. In a preferred embodiment, the candidate bioactive agent is labelled, and binding determined directly. For example, this may be done by attaching all or a portion of the Exo1 or Exo2 protein to a solid support, adding a labelled candidate agent (for example a fluorescent label), washing off excess reagent, and determining whether the label is present on the solid support. Various blocking and washing steps may be utilized as is known in the art.

By "labeled" herein is meant that the compound is either directly or indirectly labeled with a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the proteins (or proteinaceous candidate agents) may be labeled at tyrosine positions using $^{125}$I, or with fluorophores. Alternatively, more than one component may be labeled with different labels; using $^{125}$I for the proteins, for example, and a fluorophor for the candidate agents.

In a preferred embodiment, the binding of the candidate bioactive agent is determined through the use of competitive binding assays. In this embodiment, the competitor is a binding moiety known to bind to the target molecule (i.e. Exo1 or Exo2), such as an antibody, peptide, binding partner, ligand, etc. Under certain circumstances, there may be competitive binding as between the bioactive agent and the binding moiety, with the binding moiety displacing the bioactive agent.

In one embodiment, the candidate bioactive agent is labeled. Either the candidate bioactive agent, or the competitor, or both, is added first to the protein for a time sufficient to allow binding, if present. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate bioactive agent. Displacement of the competitor is an indication that the candidate bioactive agent is binding to the Exo1 or Exo2 protein and thus is capable of binding to, and potentially modulating, the activity of the Exo1 or Exo2 protein. In this embodiment, either component can be labeled. Thus, for example, if the competitor is labeled, the presence of label in the wash solution indicates displacement by the agent. Alternatively, if the candidate bioactive agent is labeled, the presence of the label on the support indicates displacement.

In an alternative embodiment, the candidate bioactive agent is added first, with incubation and washing, followed by the competitor. The absence of binding by the competitor may indicate that the bioactive agent is bound to the Exo1 or Exo2 protein with a higher affinity.

Thus, if the candidate bioactive agent is labeled, the presence of the label on the support, coupled with a lack of competitor binding, may indicate that the candidate agent is capable of binding to the Exo1 or Exo2 protein.

In a preferred embodiment, the methods comprise differential screening to identity bioactive agents that are capable of modulating the activitity of an exocytotic protein. In this embodiment, the methods comprise combining an Exo1 or Exo2 protein and a competitor in a first sample. A second sample comprises a candidate bioactive agent, an Exo1 or Exo2 protein and a competitor. The binding of the competitor is determined for both samples, and a change, or difference in binding between the two samples indicates the presence of an agent capable of binding to the Exo1 or Exo2 protein and potentially modulating its activity. That is, if the binding of the competitor is different in the second sample relative to the first sample, the agent is capable of binding to the Exo1 or Exo2 protein.

Alternatively, a preferred embodiment utilizes differential screening to identify drug candidates that bind to the native exocytotic protein, but cannot bind to modified exocytotic proteins. The structure of the exocytotic protein may be modeled, and used in rational drug design to synthesize agents that interact with that site. Drug candidates that affect exocytotic bioactivity are also identified by screening drugs for the ability to either enhance or reduce the activity of the protein.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Screening for agents that modulate the activity of an exocytotic protein may also be done. In a preferred embodiment, methods for screening for a bioactive agent capable of modulating the activity of Exo1 or Exo2 comprise the steps of adding a candidate bioactive agent to a sample of Exo1 or Exo2, as above, and determining an alteration in the biological activity of Exo1 or Exo2. "Modulating the activity of Exo1 or Exo2" includes an increase in activity, a decrease in activity, or a change in the type or kind of activity present. Thus, in this embodiment, the candidate agent should both bind to Exo1 or Exo2 (although this may not be necessary), and alter its biological or biochemical activity as defined herein. The methods include both in vitro screening methods, as are generally outlined above, and in vivo screening of cells for alterations in the presence, distribution, activity or amount of Exo1 or Exo2.

Thus, in this embodiment, the methods comprise combining an Exo1 or Exo2 sample and a candidate bioactive agent, and testing the Exo1 or Exo2 for exocytotic biological activity as is known in the art to evaluate the effect of the agent on the activity of Exo1 or Exo2. By "exocytotic biological activity" or grammatical equivalents herein is meant the ability of an exocytotic protein to modulate exocytosis and/or secretion, preferably in mast cells. By "modulate" and grammatical equivalents herein is meant inhibiting and promoting exocytosis and/or secretion. As outlined herein, exocytotic proteins modulate exocytosis. In a preferred embodiment, the activity of the Exo1 or Exo2 protein is increased; in another preferred embodiment, the activity of the Exo1 or Exo2 protein is decreased. Thus, bioactive agents that are antagonists are preferred in some embodiments, and bioactive agents that are agonists may be preferred in other embodiments.

In a preferred embodiment, the invention provides methods for screening for bioactive agents capable of modulating the activity of an Exo1 or Exo2 protein. The methods comprise adding a candidate bioactive agent, as defined above, to a cell comprising Exo1 or Exo2 proteins. Preferred cell types include almost any cell, with cells exhibiting regulated exocytosis such as mast cells, neuronal cells, and other endocrine and exocrine cells being preferred. The cells contain a recombinant nucleic acid that encodes an Exo1 or Exo2 protein. In a preferred embodiment, a library of candidate agents are tested on a plurality of cells.

The cells are then exposed to an exocytosis agent that will induce exocytosis in control cells, i.e., cells of the same type but that do not contain the exogeneous nucleic acid encoding Exo1 or Exo2. Suitable exocytotic agents include, but are not limited to, ionomycin. Alternatively, the cells may be exposed to conditions that normally result in exocytosis.

The effect of the candidate agent on exocytosis is then evaluated, for example, as being an antagonist or agonist of the exocytotic protein. For example, if an exocytotic protein is acting to inhibit exocytosis and the candidate agent acts as an antagonist to the exocytotic protein, the cells will undergo exocytosis.

Detection of exocytosis may be done as will be appreciated by those in the art. In one embodiment, annexin is used. Annexin may be used to detect exocytosis. Annexin will bind to the secretory granules that are fusing with the plasma membrane; thus the presence of fluorescence indicates that annexin is binding and exocytosis is occuring. Accordingly, annexin can be used as an affinity ligand, and attached to a solid support such as a bead, a surface, etc. and used to pull out cells that are undergoing exocytosis. Similarly, annexin can be coupled to a fluorescent dye such as PerCP, and then used as the basis of a fluorescent-activated cell sorting (FACS) separation.

In this way, bioactive agents are identified. Compounds with pharmacological activity are able to enhance or interfere with the activity of the Exo1 or Exo2 protein. The compounds having the desired pharmacological activity may be administered in a physiologically acceptable carrier to a host, as previously described. The agents may be administered in a variety of ways, orally, parenterally e.g., subcutaneously, intraperitoneally, intravascularly, etc. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Without being bound by theory, it appears that Exo1 and Exo2 are an important proteins in exocytosis. Accordingly, disorders based on mutant or variant Exo1 or Exo2 genes may be determined. In one embodiment, the invention provides methods for identifying cells containing variant Exo1 or Exo2 genes comprising determining all or part of the sequence of at least one endogeneous Exo1 or Exo2 genes in a cell. As will be appreciated by those in the art, this may be done using any number of sequencing techniques. In a preferred embodiment, the invention provides methods of identifying the Exo1 or Exo2 genotype of an individual comprising determining all or part of the sequence of at least one Exo1 or Exo2 gene of the individual. This is generally done in at least one tissue of the individual, and may include the evaluation of a number of tissues or different samples of the same tissue. The method may include comparing the sequence of the sequenced Exo1 or Exo2 gene to a known Exo1 or Exo2 gene, i.e. a wild-type gene.

The sequence of all or part of the Exo1 or Exo2 gene can then be compared to the sequence of a known Exo1 or Exo2 gene to determine if any differences exist. This can be done using any number of known homology programs, for example, as described herein, etc. In a preferred embodiment, the presence of a difference in the sequence between the Exo1 or Exo2 gene of the patient and the known Exo1 or Exo2 gene is indicative of a disease state or a propensity for a disease state, as outlined herein.

The present discovery relating to the role of Exo1 and Exo2 in exocytosis thus provides methods for inducing or preventing exocytosis in cells. In a preferred embodiment, the Exo1 or Exo2 proteins, and particularly Exo1 or Exo2 fragments, are useful in the study or treatment of conditions which are mediated by exocytosis, i.e. to diagnose, treat or prevent exocytosis-mediated disorders. Thus, "exocytosis mediated disorders" or "disease state" include conditions involving inflammation mediated by the release of certain compounds such as histamine, or inappropriate or undesirable release of compounds via exocytosis.

Thus, in one embodiment, methods of modulating exocytosis in cells or organisms are provided. In one embodiment, the methods comprise administering to a cell an anti-Exo1 or anti-Exo2 antibody that reduces or eliminates the biological activity of the corresponding endogeneous Exo1 or Exo2 protein. Alternatively, the methods comprise administering to a cell or organism a recombinant nucleic acid encoding an Exo1 or Exo2 protein. As will be appreciated by those in the art, this may be accomplished in any number of ways. In a preferred embodiment, the activity of Exo1 or Exo2 is increased by increasing the amount of Exo1 or Exo2 in the cell, for example by overexpressing the endogeneous Exo1 or Exo2 or by administering a gene encoding Exo1 or Exo2, using known gene-therapy techniques, for example. In a preferred embodiment, the gene therapy techniques include the incorporation of the exogeneous gene using enhanced homologous recombination (EHR), for example as described in PCT/US93/03868, hereby incorporated by reference in its entirety.

In one embodiment, the invention provides methods for diagnosing an exocytosis related condition in an individual. The methods comprise measuring the activity of an exocytotic protein in a tissue from the individual or patient, which may include a measurement of the amount or specific activity of Exo1 and/or Exo2. This activity is compared to the activity of Exo1 and/or Exo2 from either a unaffected second individual or from an unaffected tissue from the first individual. When these activities are different, the first individual may be at risk for an exocytosis mediated disorder.

In one embodiment, the Exo1 or Exo2 proteins of the present invention may be used to generate polyclonal and monoclonal antibodies to the Exo1 or Exo2 proteins, which are useful as described herein. Similarly, the Exo1 or Exo2 proteins can be coupled, using standard technology, to affinity chromatography columns. These columns may then be used to purify Exo1 or Exo2 antibodies. In a preferred embodiment, the antibodies are generated to epitopes unique to the Exo1 or Exo2 protein; that is, the antibodies show little or no cross-reactivity to other proteins. These antibodies find use in a number of applications. For example, the Exo1 or Exo2 antibodies may be coupled to standard affinity chromatography columns and used to purify Exo2 proteins. The antibodies may also be used as blocking polypeptides, as outlined above, since they will specifically bind to the Exo1 or Exo2 protein.

In one embodiment, a therapeutically effective dose of an Exo1 or Exo2 is administered to a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for Exo1 or Exo2 degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

The administration of the Exo1 or Exo2 proteins of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the Exo1 or Exo2 may be directly applied as a solution or spray.

The pharmaceutical compositions of the present invention comprise an Exo1 or Exo2 protein in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuiric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

All references cited herein are expressly incorporated by reference in their entirety.

We claim:

1. A method of screening for a bioactive agent capable of binding to an exocytotic protein, said protein having the amino acid sequence of SEQ ID NO:7, said protein having exocytotic biological activity, and said method comprising combining said exocytotic protein and a candidate bioactive agent, and determining the binding of said candidate agent to said exocytotic protein.

2. A method for screening for a bioactive agent capable of modulating the activity of an exocytotic protein, said method comprising the steps of:

a) adding a candidate bioactive agent to a cell comprising a recombinant nucleic acid encoding an exocytotic protein having the amino acid sequence of SEQ ID NO:7; and b) determining the effect of the candidate bioactive agent on exocytosis.

3. A method according to claim 1 or 2, further comprising adding a competitor known to bind to said exocytotic protein.

4. A method according to claim 2, further comprising, exposing said cells to an exocytosis agent.

5. A method according to claim 4, wherein said exocytosis agent is ionomycin.

6. A method according to claim 2, wherein a library of candidate bioactive agents are added to a plurality of cells comprising a recombinant nucleic acid encoding an exocytotic protein.

7. A method according to claim 2 further comprising adding a labeling agent that labels exocytotic cells.

8. A method according to claim 7, wherein said labeling agent is annexin.

9. A method according to claim 8 further comprising separating the exocytotic cells from the non-exocytotic cells.

10. A method according to claim 1 or 2 wherein said exocytotic protein is fused to a heterologous polypeptide comprising green fluorescent protein.

11. A method according to claim 1 wherein said exocytotic protein or said candidate bioactive agent is non-diffusably bound to an insoluble support having isolated sample receiving areas.

12. A method according to claim 1 or 2 wherein said candidate bioactive agent is an organic molecule.

* * * * *

SEQUENCE LISTING

<160> NUMBER OF SEQ ID NOS: 16

<210> SEQ ID NO 1
<211> LENGTH: 357
<212> TYPE: DNA
<213> ORGANISM: Mouse
<220> FEATURE:

-continued

```
<221> NAME/KEY: CDS
<222> LOCATION: (1)..(357)

<400> SEQUENCE: 1 atg ttg aag gag tcc cag aag ctg cac tat gtt gtg act gaa gtt caa         48
Met Leu Lys Glu Ser Gln Lys Leu His Tyr Val Val Thr Glu Val Gln
 1               5                  10                  15 ggc ccc agc att acc gtg gag ttc tct gat tgc aaa gct tct ctc cag         96
Gly Pro Ser Ile Thr Val Glu Phe Ser Asp Cys Lys Ala Ser Leu Gln
            20                  25                  30 ctt ccg atg gaa aag gcc att gag acc gcc ctg gac tgc ctg aaa agt        144
Leu Pro Met Glu Lys Ala Ile Glu Thr Ala Leu Asp Cys Leu Lys Ser
        35                  40                  45 gcc aac aca gag ccc tac tac cgg agg cag gca tgg gag gtg atc agg        192
Ala Asn Thr Glu Pro Tyr Tyr Arg Arg Gln Ala Trp Glu Val Ile Arg
    50                  55                  60 tgc ttc ctg gta gcc atg atg agc ctg gag gac aac aag cat gcg ctt        240
Cys Phe Leu Val Ala Met Met Ser Leu Glu Asp Asn Lys His Ala Leu
65                  70                  75                  80 tac cag ctg ctg gcg cac ccc aac ttt aca gaa aag acc att ccc aat        288
Tyr Gln Leu Leu Ala His Pro Asn Phe Thr Glu Lys Thr Ile Pro Asn
                85                  90                  95 gtc atc ata tca cat cgc tac aaa gca cag gac act cca gcc cgg gac        336
Val Ile Ile Ser His Arg Tyr Lys Ala Gln Asp Thr Pro Ala Arg Asp
            100                 105                 110 tca cgc ggc cgc tcg acg ata                                            357
Ser Arg Gly Arg Ser Thr Ile
        115

<210> SEQ ID NO 2
<211> LENGTH: 119
<212> TYPE: PRT
<213> ORGANISM: Mouse

<400> SEQUENCE: 2

Met Leu Lys Glu Ser Gln Lys Leu His Tyr Val Val Thr Glu Val Gln
 1               5                  10                  15

Gly Pro Ser Ile Thr Val Glu Phe Ser Asp Cys Lys Ala Ser Leu Gln
            20                  25                  30

Leu Pro Met Glu Lys Ala Ile Glu Thr Ala Leu Asp Cys Leu Lys Ser
        35                  40                  45

Ala Asn Thr Glu Pro Tyr Tyr Arg Arg Gln Ala Trp Glu Val Ile Arg
    50                  55                  60

Cys Phe Leu Val Ala Met Met Ser Leu Glu Asp Asn Lys His Ala Leu
65                  70                  75                  80

Tyr Gln Leu Leu Ala His Pro Asn Phe Thr Glu Lys Thr Ile Pro Asn
                85                  90                  95

Val Ile Ile Ser His Arg Tyr Lys Ala Gln Asp Thr Pro Ala Arg Asp
            100                 105                 110

Ser Arg Gly Arg Ser Thr Ile
        115

<210> SEQ ID NO 3
<211> LENGTH: 54
<212> TYPE: PRT
<213> ORGANISM: Mouse

<400> SEQUENCE: 3

Glu Val Gln Gly Pro Ser Ile Thr Val Glu Phe Ser Lys Cys Lys Ala
 1               5                  10                  15
```

```
Ser Leu Gln Leu Pro Met Glu Lys Ala Ile Glu Thr Ala Leu Asp Cys
             20                  25                  30

Leu Lys Ser Ala Asn Thr Glu Pro Tyr Tyr Arg Arg Gln Ala Trp Glu
         35                  40                  45

Val Ile Arg Cys Phe Leu
     50

<210> SEQ ID NO 4
<211> LENGTH: 54
<212> TYPE: PRT
<213> ORGANISM: Mouse

<400> SEQUENCE: 4

Glu Val Gln Glu Asp Phe Val Phe Ser Lys Tyr Arg His Arg Ala Leu
 1               5                  10                  15

Leu Leu Pro Glu Leu Leu Glu Gly Val Leu Gln Ile Leu Ile Cys Cys
             20                  25                  30

Leu Gln Ser Ala Ala Ser Asn Pro Phe Tyr Phe Ser Gln Ala Met Asp
         35                  40                  45

Leu Val Gln Glu Phe Ile
     50

<210> SEQ ID NO 5
<211> LENGTH: 192
<212> TYPE: PRT
<213> ORGANISM: Rat
<220> FEATURE:
<221> NAME/KEY: UNSURE
<222> LOCATION: (5)
<223> OTHER INFORMATION: The xaa at position 5 represents an unknown
      amino acid.
<221> NAME/KEY: UNSURE
<222> LOCATION: (27)
<223> OTHER INFORMATION: The xaa at position 27 represents any unknown
      amino acid.

<400> SEQUENCE: 5

Met Leu Leu Gly Xaa Ser Gly Val Gly Lys Thr Cys Phe Leu Ile Gln
 1               5                  10                  15

Phe Lys Asp Gly Ala Phe Leu Ser Gly Thr Xaa Ile Ala Thr Val Gly
             20                  25                  30

Ile Asp Phe Arg Asn Lys Val Val Thr Val Asp Gly Ser Arg Val Lys
         35                  40                  45

Leu Gln Ile Trp Asp Thr Ala Gly Gln Glu Arg Phe Arg Ser Val Thr
     50                  55                  60

His Ala Tyr Tyr Arg Asp Ala Gln Ala Leu Leu Leu Leu Tyr Asp Thr
 65                  70                  75                  80

Ile Asn Gln Ser Ser Phe Asp Asn Ile Arg Ala Trp Leu Thr Glu Ile
                 85                  90                  95

His Glu Tyr Ala Arg Gln Arg Asp Val Val Ile Met Leu Gly Asn Lys
             100                 105                 110

Ala Asp Val Ser Ser Glu Arg Val Ile Arg Ser Glu Asp Gly Glu Thr
         115                 120                 125

Leu Ala Arg Glu Tyr Gly Val Pro Phe Met Glu Thr Ser Ala Lys Thr
     130                 135                 140

Gly Met Asn Val Glu Leu Ala Phe Leu Ala Ile Ala Lys Glu Leu Lys
145                 150                 155                 160

Tyr Arg Ala Gly Arg Gln Pro Asp Glu Pro Ser Phe Gln Ile Arg Asp
                 165                 170                 175
```

```
Tyr Val Glu Ser Gln Lys Lys Arg Arg Ser Ser Cys Cys Ser Phe Val
        180                 185                 190
```

<210> SEQ ID NO 6
<211> LENGTH: 842
<212> TYPE: DNA
<213> ORGANISM: Mouse
<220> FEATURE:
<221> NAME/KEY: unsure
<222> LOCATION: (3)
<223> OTHER INFORMATION: The n at position 3 represents an unknown.
<221> NAME/KEY: unsure
<222> LOCATION: (6)..(8)
<223> OTHER INFORMATION: The n at positions 6 through 8 represents an
      unknown.
<221> NAME/KEY: unsure
<222> LOCATION: (12)
<223> OTHER INFORMATION: The n at position 12 represents an unknown.
<221> NAME/KEY: unsure
<222> LOCATION: (14)..(15)
<223> OTHER INFORMATION: The n at positions 14 through 15 represents an
      unknown.
<221> NAME/KEY: unsure
<222> LOCATION: (17)..(18)
<223> OTHER INFORMATION: The n at positions 17 through 18 represents an
      unknown.
<221> NAME/KEY: unsure
<222> LOCATION: (22)
<223> OTHER INFORMATION: The n at position 22 represents an unknown.
<221> NAME/KEY: unsure
<222> LOCATION: (25)
<223> OTHER INFORMATION: The n at position 25 represents an unknown.
<221> NAME/KEY: unsure
<222> LOCATION: (726)
<223> OTHER INFORMATION: The n at position 726 represents an unknown.
<221> NAME/KEY: unsure
<222> LOCATION: (823)
<223> OTHER INFORMATION: The n at position 823 represents an unknown.
<221> NAME/KEY: unsure
<222> LOCATION: (108)
<223> OTHER INFORMATION: The n at position 108 represents an unknown.
<221> NAME/KEY: unsure
<222> LOCATION: (138)
<223> OTHER INFORMATION: The n at position 138 represents an unknown.
<221> NAME/KEY: unsure
<222> LOCATION: (204)
<223> OTHER INFORMATION: The n at position 204 represents an unknown.

<400> SEQUENCE: 6

```
aanccnnnta gnanngnncg gnganatgaa tggcacacca ggagcttgct accgcttggg      60
gatggcgagg ccctgagcgc tccccgccct tcagcccgaa ctacgatntc accggcaagg    120
gtgatgcttc ttggagantc gggcgtcggc aaaacctgtt tcctgatcca attcaaagac    180
ggggccttcc tgtccggaac cttnatagcc accgtcggca tagacttcag gaataaagtg    240
gtgacagtgg atggttccag ggtgaagctt cagatctggg acactgcagg acaggagcgc    300
ttccgcagtg tgacccatgc ttattaccga gatgctcagg ctttgctcct gttgtatgac    360
atcaccaacc agtcctcttt tgacaacatc agggcctggc tcacagagat tcatgagtat    420
gcccagaggg acgtggtgat tatgcttcta ggcaacaagg ccgatgtaag cagcgaaagg    480
gtgatccgtt ctgaagatgg agagacactg gccaggaat atggtgttcc tttcatggag     540
accagtgcca agactggcat gaacgtggag ttggcctttc tggcaattgc caaggaactg    600
aaataccgtg cagggaggca gcctgatgag cccagcttcc agatccgaga ctatgtggag    660
tcccagaaga agcgctccag ctgctgctcc tttgtgtgac cccctagggg ctaagaggag    720
gcccanagac ccttggggat gcagtactcc aactgccaca ccaactagga gaagctgggg    780
gctcaatggg cagcccctgc caagggagta gccattaccc tangttcttt agcttccctg    840
``` ca                                                                                                    842

<210> SEQ ID NO 7
<211> LENGTH: 190
<212> TYPE: PRT
<213> ORGANISM: Mouse

<400> SEQUENCE: 7

Met Leu Val Gly Asp Ser Gly Val Gly Lys Thr Cys Leu Leu Val Arg
 1               5                  10                  15

Phe Lys Asp Gly Ala Phe Leu Ala Gly Thr Phe Ile Ser Thr Val Gly
            20                  25                  30

Ile Asp Phe Arg Asn Lys Val Leu Asp Val Asp Gly Met Lys Val Lys
        35                  40                  45

Leu Gln Ile Trp Asp Thr Ala Gly Gln Glu Arg Phe Arg Ser Val Thr
    50                  55                  60

His Ala Tyr Tyr Arg Asp Ala His Ala Leu Leu Leu Tyr Asp Ile
65                  70                  75                  80

Thr Asn Lys Asp Ser Phe Asp Asn Ile Gln Ala Trp Leu Thr Glu Ile
                85                  90                  95

Gln Glu Tyr Ala Gln Gln Asp Val Val Leu Met Leu Gly Asn Lys
            100                 105                 110

Val Asp Ser Thr Gln Glu Arg Val Val Lys Arg Glu Asp Gly Glu Lys
        115                 120                 125

Leu Ala Lys Glu Tyr Gly Leu Pro Phe Met Glu Thr Ser Ala Lys Ser
    130                 135                 140

Gly Leu Asn Val Asp Leu Ala Phe Thr Ala Ile Ala Lys Glu Leu Lys
145                 150                 155                 160

Gln Arg Ser Thr Lys Ala Pro Ser Glu Pro Arg Phe Arg Leu His Asp
                165                 170                 175

Tyr Val Lys Arg Glu Gly Arg Gly Val Ser Cys Cys Pro Leu
            180                 185                 190

<210> SEQ ID NO 8
<211> LENGTH: 191
<212> TYPE: PRT
<213> ORGANISM: Artificial Sequence
<220> FEATURE:
<223> OTHER INFORMATION: Description of Artificial Sequence: Consensus
<221> NAME/KEY: UNSURE
<222> LOCATION: (3)
<223> OTHER INFORMATION: The xaa at position 3 represents either Leucine
      or Valine.
<221> NAME/KEY: UNSURE
<222> LOCATION: (5)
<223> OTHER INFORMATION: The xaa at position 5 represents a non-
      conserved amino acid.
<221> NAME/KEY: UNSURE
<222> LOCATION: (13)
<223> OTHER INFORMATION: The xaa at position 13 represents a non-
      conserved amino acid.
<221> NAME/KEY: UNSURE
<222> LOCATION: (15)
<223> OTHER INFORMATION: The xaa at position 15 represents either
      Isoleucine or Valine.
<221> NAME/KEY: UNSURE
<222> LOCATION: (16)
<223> OTHER INFORMATION: The xaa at position 16 represents either
      Glutamine or Arginine.
<221> NAME/KEY: UNSURE
<222> LOCATION: (24)
<223> OTHER INFORMATION: The xaa at position 24 represents either Serine
      or Alanine.
<221> NAME/KEY: UNSURE

```
<222> LOCATION: (27)
<223> OTHER INFORMATION: The xaa at position 27 represents an unknown
      amino acid.
<221> NAME/KEY: UNSURE
<222> LOCATION: (29)
<223> OTHER INFORMATION: The xaa at position 29 represetns either
      Alanine or Serine.
<221> NAME/KEY: UNSURE
<222> LOCATION: (40)
<223> OTHER INFORMATION: The xaa at position 40 represents either Valine
      or Leucine.
<221> NAME/KEY: UNSURE
<222> LOCATION: (41)
<223> OTHER INFORMATION: The xaa at position 41 represents a non-
      conserved amino acid.
<221> NAME/KEY: UNSURE
<222> LOCATION: (45)
<223> OTHER INFORMATION: The xaa at position 45 represents a non-
      conserved amino acid.
<221> NAME/KEY: UNSURE
<222> LOCATION: (46)
<223> OTHER INFORMATION: The xaa at position 46 represents either
      Arginine or Lysine.
<221> NAME/KEY: UNSURE
<222> LOCATION: (72)
<223> OTHER INFORMATION: The xaa at position 72 represents a non-
      conserved amino acid.
<221> NAME/KEY: UNSURE
<222> LOCATION: (83)
<223> OTHER INFORMATION: The xaa at position 83 represents either
      Glutamine or Lysine.
<221> NAME/KEY: UNSURE
<222> LOCATION: (84)
<223> OTHER INFORMATION: The xaa at position 84 represents a non-
      conserved amino acid.
<221> NAME/KEY: UNSURE
<222> LOCATION: (90)
<223> OTHER INFORMATION: The xaa at position 90 represents either
      Arginine or Glutamine.
<221> NAME/KEY: UNSURE
<222> LOCATION: (97)
<223> OTHER INFORMATION: The xaa at position 97 represents a non-
      conserved amino acid.
<221> NAME/KEY: UNSURE
<222> LOCATION: (102)
<223> OTHER INFORMATION: The xaa at position 102 represents either
      Arginine or Glutamine.
<221> NAME/KEY: UNSURE
<222> LOCATION: (106)
<223> OTHER INFORMATION: The xaa at position 106 represents either
      Isoleucine or Leucine.
<221> NAME/KEY: UNSURE
<222> LOCATION: (113)
<223> OTHER INFORMATION: The xaa at position 113 represents a non-
      conserved amino acid.
<221> NAME/KEY: UNSURE
<222> LOCATION: (115)
<223> OTHER INFORMATION: The xaa at position 115 represents a non-
      conserved amino acid.
<221> NAME/KEY: UNSURE
<222> LOCATION: (116)
<223> OTHER INFORMATION: The xaa at position 116 represents either a
      Serine or Threonine.
<221> NAME/KEY: UNSURE
<222> LOCATION: (117)
<223> OTHER INFORMATION: The xaa at position 117 represents a non-
      conserved amino acid.
<221> NAME/KEY: UNSURE
<222> LOCATION: (121)
<223> OTHER INFORMATION: The xaa at position 121 represents either
      Isoleucine or Valine.
<221> NAME/KEY: UNSURE
<222> LOCATION: (122)
<223> OTHER INFORMATION: The xaa at position 122 represents either
      Arginine or Lysine.
<221> NAME/KEY: UNSURE
<222> LOCATION: (123)
<223> OTHER INFORMATION: The xaa at position 123 represents a non-
      conserved amino acid.
```

-continued

```
<221> NAME/KEY: UNSURE
<222> LOCATION: (128)
<223> OTHER INFORMATION: The xaa at position 128 represents a non-
      conserved amino acid.
<221> NAME/KEY: UNSURE
<222> LOCATION: (131)
<223> OTHER INFORMATION: The xaa at position 131 represents either
      Arginine or Lysine.
<221> NAME/KEY: UNSURE
<222> LOCATION: (135)
<223> OTHER INFORMATION: The xaa at position 135 represents either
      Valine or Leucine.
<221> NAME/KEY: UNSURE
<222> LOCATION: (144)
<223> OTHER INFORMATION: The xaa at position 144 represents either
      Threonine or Serine.
<221> NAME/KEY: UNSURE
<222> LOCATION: (146)
<223> OTHER INFORMATION: The xaa at position 146 represents either
      Methionine or Leucine.
<221> NAME/KEY: UNSURE
<222> LOCATION: (149)
<223> OTHER INFORMATION: The xaa at position 149 represents either
      Glutamic acid or Aspartic acid.
<221> NAME/KEY: UNSURE
<222> LOCATION: (153)
<223> OTHER INFORMATION: The xaa at position 153 represents a non-
      conserved amino acid.
<221> NAME/KEY: UNSURE
<222> LOCATION: (161)
<223> OTHER INFORMATION: The xaa at position 161 represents a non-
      conserved amino acid.
<221> NAME/KEY: UNSURE
<222> LOCATION: (163)
<223> OTHER INFORMATION: The xaa at position 163 represents Alanine or
      Serine.
<221> NAME/KEY: UNSURE
<222> LOCATION: (164)
<223> OTHER INFORMATION: The xaa at position 164 represents a non-
      conserved amino acid.
<221> NAME/KEY: UNSURE
<222> LOCATION: (165)
<223> OTHER INFORMATION: The xaa at position 165 represents Arginine or
      Lysine.
<221> NAME/KEY: UNSURE
<222> LOCATION: (166)
<223> OTHER INFORMATION: The xaa at position 166 represents a non-
      conserved amino acid.
<221> NAME/KEY: UNSURE
<222> LOCATION: (168)
<223> OTHER INFORMATION: The xaa at position 168 represents a non-
      conserved amino acid.
<221> NAME/KEY: UNSURE
<222> LOCATION: (171)
<223> OTHER INFORMATION: The xaa at position 171 represents a non-
      conserved amino acid.
<221> NAME/KEY: UNSURE
<222> LOCATION: (173)
<223> OTHER INFORMATION: The xaa at position 173 represents a Glutamine
      or Arginine.
<221> NAME/KEY: UNSURE
<222> LOCATION: (174)
<223> OTHER INFORMATION: The xaa at position 174 represents either
      Isoleucine or Leucine.
<221> NAME/KEY: UNSURE
<222> LOCATION: (175)
<223> OTHER INFORMATION: The xaa at position 175 represents a non-
      conserved amino acid.
<221> NAME/KEY: UNSURE
<222> LOCATION: (179)
<223> OTHER INFORMATION: The xaa at position 179 represents Glutamic
      acid or Lysine.
<221> NAME/KEY: UNSURE
<222> LOCATION: (180)
<223> OTHER INFORMATION: The xaa at position 180 represents a non-
      conserved amino acid.
<221> NAME/KEY: UNSURE
<222> LOCATION: (181)
<223> OTHER INFORMATION: The xaa at position 181 represents either
```

```
        Glutamine or Glutamic acid.
<221> NAME/KEY: UNSURE
<222> LOCATION: (182)
<223> OTHER INFORMATION: The xaa at position 182 represents a non-
      conserved amino acid.
<221> NAME/KEY: UNSURE
<222> LOCATION: (183)
<223> OTHER INFORMATION: The xaa at position 183 represents either
      Lysine or Arginine.
<221> NAME/KEY: UNSURE
<222> LOCATION: (184)
<223> OTHER INFORMATION: The xaa at position 184 represents a non-
      conserved amino acid.
<221> NAME/KEY: UNSURE
<222> LOCATION: (185)
<223> OTHER INFORMATION: The xaa at position 185 represents either
      Serine or Valine.

<400> SEQUENCE: 8

Met Leu Xaa Gly Xaa Ser Gly Val Gly Lys Thr Cys Xaa Leu Xaa Xaa
  1               5                  10                  15

Phe Lys Asp Gly Ala Phe Leu Xaa Gly Thr Xaa Ile Xaa Thr Val Gly
                 20                  25                  30

Ile Asp Phe Arg Asn Lys Val Xaa Xaa Val Asp Gly Xaa Xaa Val Lys
             35                  40                  45

Leu Gln Ile Trp Asp Thr Ala Gly Gln Glu Arg Phe Arg Ser Val Thr
 50                  55                  60

His Ala Tyr Tyr Arg Asp Ala Xaa Ala Leu Leu Leu Tyr Asp Ile
 65                  70                  75                  80

Thr Asn Xaa Xaa Ser Phe Asp Asn Ile Xaa Ala Trp Leu Thr Glu Ile
                 85                  90                  95

Xaa Glu Tyr Ala Gln Xaa Asp Val Val Xaa Met Leu Leu Gly Asn Lys
             100                 105                 110

Xaa Asp Xaa Xaa Xaa Glu Arg Val Xaa Xaa Xaa Glu Asp Gly Glu Xaa
         115                 120                 125

Leu Ala Xaa Glu Tyr Gly Xaa Pro Phe Met Glu Thr Ser Ala Lys Xaa
    130                 135                 140

Gly Xaa Asn Val Xaa Leu Ala Phe Xaa Ala Ile Ala Lys Glu Leu Lys
145                 150                 155                 160

Xaa Arg Xaa Xaa Xaa Xaa Pro Xaa Glu Pro Xaa Phe Xaa Xaa Xaa Asp
                 165                 170                 175

Tyr Val Xaa Xaa Xaa Xaa Xaa Xaa Ser Cys Cys Xaa Xaa Xaa
             180                 185                 190

<210> SEQ ID NO 9
<211> LENGTH: 32
<212> TYPE: PRT
<213> ORGANISM: Mouse

<400> SEQUENCE: 9

Leu Glu Gly Val Leu Gln Leu Leu Ile Ser Cys Leu Gln Ser Ala Ala
  1               5                  10                  15

Ser Asn Pro Phe Tyr Phe Ser Gln Ala Met Asp Leu Val Gln Glu Phe
                 20                  25                  30

<210> SEQ ID NO 10
<211> LENGTH: 32
<212> TYPE: PRT
<213> ORGANISM: Mouse

<400> SEQUENCE: 10

Met Glu Lys Ala Ile Glu Thr Ala Leu Asp Cys Leu Lys Ser Ala Asn
```

-continued

```
                 1               5                  10                 15
           Thr Glu Pro Tyr Tyr Arg Arg Gln Ala Trp Glu Val Ile Arg Cys Phe
                           20                 25                 30
```

<210> SEQ ID NO 11
<211> LENGTH: 202
<212> TYPE: PRT
<213> ORGANISM: Rat

<400> SEQUENCE: 11

```
Phe Ser Pro Asn Tyr Asp Leu Thr Gly Lys Val Met Leu Leu Gly Asp
 1               5                  10                 15

Ser Gly Val Gly Lys Thr Cys Phe Leu Ile Gln Phe Lys Asp Gly Ala
            20                  25                 30

Phe Leu Ser Gly Thr Phe Ile Ala Thr Val Gly Ile Asp Phe Arg Asn
        35                  40                  45

Lys Val Val Thr Val Asp Gly Ala Arg Val Lys Leu Gln Ile Trp Asp
 50                  55                  60

Thr Ala Gly Gln Glu Arg Phe Arg Ser Val Thr His Ala Tyr Tyr Arg
 65                  70                  75                  80

Asp Ala Gln Ala Leu Leu Leu Leu Tyr Asp Ile Thr Asn Gln Ser Ser
                85                  90                  95

Phe Asp Asn Ile Arg Ala Trp Leu Thr Glu Ile His Glu Tyr Ala Gln
            100                 105                 110

Arg Asp Val Val Ile Met Leu Leu Gly Asn Lys Ala Asp Val Ser Ser
        115                 120                 125

Glu Arg Val Ile Arg Ser Glu Asp Gly Glu Thr Leu Ala Arg Glu Tyr
    130                 135                 140

Gly Val Pro Phe Met Glu Thr Ser Ala Lys Thr Gly Met Asn Val Glu
145                 150                 155                 160

Leu Ala Phe Leu Ala Ile Ala Lys Glu Leu Lys Tyr Arg Ala Gly Arg
                165                 170                 175

Gln Pro Asp Glu Pro Ser Phe Gln Ile Arg Asp Tyr Val Glu Ser Gln
            180                 185                 190

Lys Lys Arg Ser Ser Cys Cys Ser Phe Val
        195                 200
```

<210> SEQ ID NO 12
<211> LENGTH: 203
<212> TYPE: PRT
<213> ORGANISM: Mouse
<220> FEATURE:
<221> NAME/KEY: UNSURE
<222> LOCATION: (34)
<223> OTHER INFORMATION: The xaa at position 34 represents an unknown
      amino acid.

<400> SEQUENCE: 12

```
Met Ala Lys Thr Tyr Asp Tyr Leu Phe Lys Leu Leu Leu Ile Gly Asp
 1               5                  10                 15

Ser Gly Val Gly Lys Thr Cys Val Leu Phe Arg Phe Ser Glu Asp Ala
            20                  25                 30

Phe Xaa Asn Ser Thr Phe Ile Ser Thr Ile Gly Ile Asp Phe Lys Ile
        35                  40                  45

Arg Thr Ile Glu Leu Asp Gly Lys Arg Ile Lys Leu Gln Ile Trp Asp
 50                  55                  60

Thr Ala Gly Gln Glu Arg Phe Arg Thr Ile Thr Thr Ala Tyr Tyr Arg
 65                  70                  75                  80
```

```
Gly Ala Met Gly Ile Met Leu Val Tyr Asp Ile Thr Asn Glu Lys Ser
                85                  90                  95

Phe Asp Asn Ile Arg Asn Trp Ile Arg Asn Ile Glu Glu His Ala Ser
            100                 105                 110

Ala Asp Val Glu Lys Met Ile Leu Gly Asn Lys Cys Asp Val Asn Asp
        115                 120                 125

Lys Arg Gln Val Ser Lys Glu Arg Gly Glu Lys Leu Ala Leu Asp Tyr
    130                 135                 140

Gly Ile Lys Phe Met Glu Thr Ser Ala Lys Ala Asn Ile Asn Val Glu
145                 150                 155                 160

Asn Ala Phe Phe Thr Leu Ala Arg Asp Ile Lys Ala Lys Met Asp Lys
                165                 170                 175

Asn Trp Lys Ala Thr Ala Ala Gly Ser Ser His Gly Val Lys Ile Thr
            180                 185                 190

Val Glu Gln Gln Lys Arg Thr Ser Phe Phe Arg
        195                 200
```

<210> SEQ ID NO 13
<211> LENGTH: 203
<212> TYPE: PRT
<213> ORGANISM: Artificial Sequence
<220> FEATURE:
<223> OTHER INFORMATION: Description of Artificial Sequence: Consensus
<221> NAME/KEY: UNSURE
<222> LOCATION: (1)
<223> OTHER INFORMATION: The xaa at position 1 represents either
    Phenyalanine or Methionine.
<221> NAME/KEY: UNSURE
<222> LOCATION: (2)
<223> OTHER INFORMATION: The xaa at position 2 represents either Serine
    or Alanine.
<221> NAME/KEY: UNSURE
<222> LOCATION: (3)
<223> OTHER INFORMATION: The xaa at position 3 represents a non-
    conserved amino acid.
<221> NAME/KEY: UNSURE
<222> LOCATION: (4)
<223> OTHER INFORMATION: The xaa at position 4 represents either
    Asparagine or Threonine.
<221> NAME/KEY: UNSURE
<222> LOCATION: (7)..(9)
<223> OTHER INFORMATION: The xaa at positions 7 through 9 represents a
    non-conserved amino acid.
<221> NAME/KEY: UNSURE
<222> LOCATION: (11)
<223> OTHER INFORMATION: The xaa at position 11 represents either
    Valine or Leucine.
<221> NAME/KEY: UNSURE
<222> LOCATION: (12)
<223> OTHER INFORMATION: The xaa at position 12 represents either
    Methionine or Leucine.
<221> NAME/KEY: UNSURE
<222> LOCATION: (14)
<223> OTHER INFORMATION: The xaa at position 14 represents either
    Leucine or Isoleucine.
<221> NAME/KEY: UNSURE
<222> LOCATION: (24)
<223> OTHER INFORMATION: The xaa at position 24 represents a non-
    conserved amino acid.
<221> NAME/KEY: UNSURE
<222> LOCATION: (26)
<223> OTHER INFORMATION: The xaa at position 26 represents either
    Isoleucine or Phenylanine.
<221> NAME/KEY: UNSURE
<222> LOCATION: (27)
<223> OTHER INFORMATION: The xaa at position 27 represents either
    Glutamine or Arginine.
<221> NAME/KEY: UNSURE
<222> LOCATION: (29)
<223> OTHER INFORMATION: The xaa at position 29 represents either

```
        Lysine or Serine.
<221> NAME/KEY: UNSURE
<222> LOCATION: (30)
<223> OTHER INFORMATION: The xaa at position 30 represents either
        Aspartic acid or Glutamic acid.
<221> NAME/KEY: UNSURE
<222> LOCATION: (31)
<223> OTHER INFORMATION: The xaa at position 31 represents either
        Glycine or Aspartic acid.
<221> NAME/KEY: UNSURE
<222> LOCATION: (34)
<223> OTHER INFORMATION: The xaa at position 34 represents a non-
        conserved amino acid.
<221> NAME/KEY: UNSURE
<222> LOCATION: (35)
<223> OTHER INFORMATION: The xaa at position 35 represents either
        Serine or Asparagine.
<221> NAME/KEY: UNSURE
<222> LOCATION: (36)
<223> OTHER INFORMATION: The xaa at position 36 represents either
        Glycine or Serine.
<221> NAME/KEY: UNSURE
<222> LOCATION: (40)
<223> OTHER INFORMATION: The xaa at position 40 represents either
        Alanine or Serine.
<221> NAME/KEY: UNSURE
<222> LOCATION: (42)
<223> OTHER INFORMATION: The xaa at position 42 represents either
        Valine or Isoleucine.
<221> NAME/KEY: UNSURE
<222> LOCATION: (47)
<223> OTHER INFORMATION: The xaa at position 47 represents either
        Arginine or Lysine.
<221> NAME/KEY: UNSURE
<222> LOCATION: (48)
<223> OTHER INFORMATION: The xaa at position 48 represents a non-
        conserved amino acid.
<221> NAME/KEY: UNSURE
<222> LOCATION: (49)
<223> OTHER INFORMATION: The xaa at position 49 represents either Lysine
        or Arginine.
<221> NAME/KEY: UNSURE
<222> LOCATION: (50)
<223> OTHER INFORMATION: The xaa at position 50 represents either Valine
        or Threonine.
<221> NAME/KEY: UNSURE
<222> LOCATION: (51)
<223> OTHER INFORMATION: The xaa at position 51 represents either Valine
        or Isoleucine.
<221> NAME/KEY: UNSURE
<222> LOCATION: (52)
<223> OTHER INFORMATION: The xaa at position 52 represents either
        Threonine or Glutamic acid.
<221> NAME/KEY: UNSURE
<222> LOCATION: (53)
<223> OTHER INFORMATION: The xaa at position 53 represents either Valine
        or Leucine.
<221> NAME/KEY: UNSURE
<222> LOCATION: (56)
<223> OTHER INFORMATION: The xaa at position 56 represents a non-
        conserved amino acid.
<221> NAME/KEY: UNSURE
<222> LOCATION: (58)
<223> OTHER INFORMATION: The xaa at position 58 represents either Valine
        or Isoleucine.
<221> NAME/KEY: UNSURE
<222> LOCATION: (73)
<223> OTHER INFORMATION: The xaa at position 73 represents either Serine
        or Threonine.
<221> NAME/KEY: UNSURE
<222> LOCATION: (74)
<223> OTHER INFORMATION: The xaa at position 74 represents either Valine
        or Isoleucine.
<221> NAME/KEY: UNSURE
<222> LOCATION: (76)
<223> OTHER INFORMATION: The xaa at position 76 represents a non-
        conserved amino acid.
<221> NAME/KEY: UNSURE
<222> LOCATION: (81)
```

-continued

```
<223> OTHER INFORMATION: The xaa at position 81 represents either
      Aspartic acid or Glycine.
<221> NAME/KEY: UNSURE
<222> LOCATION: (83)
<223> OTHER INFORMATION: The xaa at position 83 represents a non-
      conserved amino acid.
<221> NAME/KEY: UNSURE
<222> LOCATION: (84)
<223> OTHER INFORMATION: The xaa at position 84 represents either
      Alanine or Glycine.
<221> NAME/KEY: UNSURE
<222> LOCATION: (85)
<223> OTHER INFORMATION: The xaa at position 85 represents either
      Leucine or Isoleucine.
<221> NAME/KEY: UNSURE
<222> LOCATION: (86)
<223> OTHER INFORMATION: The xaa at position 86 represents either
      Methionine or Leucine.
<221> NAME/KEY: UNSURE
<222> LOCATION: (88)
<223> OTHER INFORMATION: The xaa at position 88 represents either
      Leucine or Valine.
<221> NAME/KEY: UNSURE
<222> LOCATION: (94)
<223> OTHER INFORMATION: The xaa at position 94 represents either
      Glutamine or Glutamic acid.
<221> NAME/KEY: UNSURE
<222> LOCATION: (95)
<223> OTHER INFORMATION: The xaa at position 95 represents either Serine
      or Lysine.
<221> NAME/KEY: UNSURE
<222> LOCATION: (102)
<223> OTHER INFORMATION: The xaa at position 102 represents either
      Alanine or Asparagine.
<221> NAME/KEY: UNSURE
<222> LOCATION: (104)
<223> OTHER INFORMATION: The xaa at position 104 represents either
      Leucine or Isoleucine.
<221> NAME/KEY: UNSURE
<222> LOCATION: (105)
<223> OTHER INFORMATION: The xaa at position 105 represents a non-
      conserved amino acid.
<221> NAME/KEY: UNSURE
<222> LOCATION: (106)
<223> OTHER INFORMATION: The xaa at position 106 represents either
      Asparagine or Glutamic acid.
<221> NAME/KEY: UNSURE
<222> LOCATION: (108)
<223> OTHER INFORMATION: The xaa at position 108 represents either
      Histidine or Glutamic acid.
<221> NAME/KEY: UNSURE
<222> LOCATION: (110)
<223> OTHER INFORMATION: The xaa at position 110 represents either
      Tyrosine or Histidine.
<221> NAME/KEY: UNSURE
<222> LOCATION: (112)..(113)
<223> OTHER INFORMATION: The xaa at positions 112 and 113 represents a
      non-conserved amino acid.
<221> NAME/KEY: UNSURE
<222> LOCATION: (116)..(117)
<223> OTHER INFORMATION: The xaa at positions 116 and 117 represents a
      non-conserved amino acid.
<221> NAME/KEY: UNSURE
<222> LOCATION: (119)
<223> OTHER INFORMATION: The xaa at position 119 represents either
      Leucine or Isoleucine.
<221> NAME/KEY: UNSURE
<222> LOCATION: (124)
<223> OTHER INFORMATION: The xaa at position 124 represents either
      Alanine or Cysteine.
<221> NAME/KEY: UNSURE
<222> LOCATION: (127)
<223> OTHER INFORMATION: The xaa at position 127 represents either
      Serine or Asparagine.
<221> NAME/KEY: UNSURE
<222> LOCATION: (128)
<223> OTHER INFORMATION: The xaa at position 128 represents either
      Serine or Aspartic acid.
<221> NAME/KEY: UNSURE
```

```
<222> LOCATION: (129)
<223> OTHER INFORMATION: The xaa at position 129 represents either
      Glutamic acid or Lysine.
<221> NAME/KEY: UNSURE
<222> LOCATION: (131)
<223> OTHER INFORMATION: The xaa at position 131 represents a non-
      conserved amino acid.
<221> NAME/KEY: UNSURE
<222> LOCATION: (132)
<223> OTHER INFORMATION: The xaa at position 157 represents either
      Isoleucine or Valine.
<221> NAME/KEY: UNSURE
<222> LOCATION: (133)
<223> OTHER INFORMATION: The xaa at position 133 represents either
      Arginine or Serine.
<221> NAME/KEY: UNSURE
<222> LOCATION: (134)
<223> OTHER INFORMATION: The xaa at position 134 represents either
      Serine or Lysine.
<221> NAME/KEY: UNSURE
<222> LOCATION: (136)
<223> OTHER INFORMATION: The xaa at position 136 represents a non-
      conserved amino acid.
<221> NAME/KEY: UNSURE
<222> LOCATION: (139)
<223> OTHER INFORMATION: The xaa at position 139 represents either
      Threonine or Lsyine.
<221> NAME/KEY: UNSURE
<222> LOCATION: (142)
<223> OTHER INFORMATION: The xaa at position 142 represents a non-
      conserved amino acid.
<221> NAME/KEY: UNSURE
<222> LOCATION: (143)
<223> OTHER INFORMATION: The xaa at position 143 represents either
      Glutamic acid or Aspartic acid.
<221> NAME/KEY: UNSURE
<222> LOCATION: (146)
<223> OTHER INFORMATION: The xaa at position 146 represents either
      Valine or Isoleucine.
<221> NAME/KEY: UNSURE
<222> LOCATION: (147)
<223> OTHER INFORMATION: The xaa at position 147 represents a non-
      conserved amino acid.
<221> NAME/KEY: UNSURE
<222> LOCATION: (155)
<223> OTHER INFORMATION: The xaa at position 155 represents either
      Threonine or Alanine.
<221> NAME/KEY: UNSURE
<222> LOCATION: (156)
<223> OTHER INFORMATION: The xaa at position 156 represents either
      Glycine or Asparagine.
<221> NAME/KEY: UNSURE
<222> LOCATION: (157)
<223> OTHER INFORMATION: The xaa at position 157 represents either
      Methionine or Isoleucine.
<221> NAME/KEY: UNSURE
<222> LOCATION: (161)
<223> OTHER INFORMATION: The xaa at position 161 represents a non-
      conserved amino acid.
<221> NAME/KEY: UNSURE
<222> LOCATION: (164)
<223> OTHER INFORMATION: The xaa at position 164 represents either
      Leucine or Phenylalanine.
<221> NAME/KEY: UNSURE
<222> LOCATION: (165)
<223> OTHER INFORMATION: The xaa at position 165 represents either
      Alanine or Threonine.
<221> NAME/KEY: UNSURE
<222> LOCATION: (166)
<223> OTHER INFORMATION: The xaa at position 166 represents either
      Isoleucine or Leucine.
<221> NAME/KEY: UNSURE
<222> LOCATION: (168)
<223> OTHER INFORMATION: The xaa at position 168 represents either
      Lysine or Arginine.
<221> NAME/KEY: UNSURE
<222> LOCATION: (169)
<223> OTHER INFORMATION: The xaa at position 169 represents either
      Glutamic acid or Aspartic acid.
```

-continued

```
<221> NAME/KEY: UNSURE
<222> LOCATION: (170)
<223> OTHER INFORMATION: The xaa at position 170 represents either
      Leucine or Isoleucine.
<221> NAME/KEY: UNSURE
<222> LOCATION: (172)
<223> OTHER INFORMATION: The xaa at position 172 represents a non-
      conserved amino acid.
<221> NAME/KEY: UNSURE
<222> LOCATION: (173)
<223> OTHER INFORMATION: The xaa at position 173 represents either
      Arginine or Lysine.
<221> NAME/KEY: UNSURE
<222> LOCATION: (174)
<223> OTHER INFORMATION: The xaa at position 174 represents a non-
      conserved amino acid.
<221> NAME/KEY: UNSURE
<222> LOCATION: (175)
<223> OTHER INFORMATION: The xaa at position 175 represents either
      Glycine or Aspartic acid.
<221> NAME/KEY: UNSURE
<222> LOCATION: (176)
<223> OTHER INFORMATION: The xaa at position 176 represents either
      Arginine or Lysine.
<221> NAME/KEY: UNSURE
<222> LOCATION: (177)
<223> OTHER INFORMATION: The xaa at position 177 represents either
      Glutamine or Asparagine
<221> NAME/KEY: UNSURE
<222> LOCATION: (178)
<223> OTHER INFORMATION: The xaa at position 178 represents a non-
      conserved amino acid.
<221> NAME/KEY: UNSURE
<222> LOCATION: (179)
<223> OTHER INFORMATION: The xaa at position 179 represents either
      Aspartic acid or Lysine.
<221> NAME/KEY: UNSURE
<222> LOCATION: (180)
<223> OTHER INFORMATION: The xaa at position 180 represents either
      Glutamic acid or Alanine.
<221> NAME/KEY: UNSURE
<222> LOCATION: (181)
<223> OTHER INFORMATION: The xaa at position 181 represents either
      Proline or Threonine.
<221> NAME/KEY: UNSURE
<222> LOCATION: (182)
<223> OTHER INFORMATION: The xaa at position 182 represents either
      Serine or Alanine.
<221> NAME/KEY: UNSURE
<222> LOCATION: (183)..(185)
<223> OTHER INFORMATION: The xaa at position 183 through 185 represents
      a non-conserved amino acid.
<221> NAME/KEY: UNSURE
<222> LOCATION: (186)
<223> OTHER INFORMATION: The xaa at position 186 represents either
      Arginine or Serine.
<221> NAME/KEY: UNSURE
<222> LOCATION: (187)
<223> OTHER INFORMATION: The xaa at position 187 represents either
      Aspartic acid or Histidine.
<221> NAME/KEY: UNSURE
<222> LOCATION: (188)
<223> OTHER INFORMATION: The xaa at position 188 represents a non-
      conserved amino acid.
<221> NAME/KEY: UNSURE
<222> LOCATION: (190)
<223> OTHER INFORMATION: The xaa at position 190 represents either
      Glutamic acid or Lysine.
<221> NAME/KEY: UNSURE
<222> LOCATION: (191)..(193)
<223> OTHER INFORMATION: The xaa at position 191 through 193 represents
      a non-conserved amino acid.
<221> NAME/KEY: UNSURE
<222> LOCATION: (194)
<223> OTHER INFORMATION: The xaa at position 194 represents either
      Lysine or Glutamic acid.
<221> NAME/KEY: UNSURE
<222> LOCATION: (195)
<223> OTHER INFORMATION: The xaa at position 195 represents either
```

```
            Arginine or Glutamine.
<221> NAME/KEY: UNSURE
<222> LOCATION: (196)
<223> OTHER INFORMATION: The xaa at position 196 represents a non-
      conserved amino acid.
<221> NAME/KEY: UNSURE
<222> LOCATION: (197)
<223> OTHER INFORMATION: The xaa at position 197 represents either
      Serine or Lysine.
<221> NAME/KEY: UNSURE
<222> LOCATION: (198)..(199)
<223> OTHER INFORMATION: The xaa at positions 198 and 199 represents a
      non-conserved amino acid.
<221> NAME/KEY: UNSURE
<222> LOCATION: (202)
<223> OTHER INFORMATION: The xaa at position 202 represents a non-
      conserved amino acid.
<221> NAME/KEY: UNSURE
<222> LOCATION: (203)
<223> OTHER INFORMATION: The xaa at position 203 represents either
      Arginine or no amino acid.

<400> SEQUENCE: 13

Xaa Xaa Xaa Xaa Tyr Asp Xaa Xaa Lys Xaa Xaa Leu Xaa Gly Asp
  1               5                  10                  15

Ser Gly Val Gly Lys Thr Cys Xaa Leu Xaa Xaa Phe Xaa Xaa Xaa Ala
             20                  25                  30

Phe Xaa Xaa Xaa Thr Phe Ile Xaa Thr Xaa Gly Ile Asp Phe Xaa Xaa
         35                  40                  45

Xaa Xaa Xaa Xaa Xaa Asp Gly Xaa Arg Xaa Lys Leu Gln Ile Trp Asp
     50                  55                  60

Thr Ala Gly Gln Glu Arg Phe Arg Xaa Xaa Thr Xaa Ala Tyr Tyr Arg
 65                  70                  75                  80

Xaa Ala Xaa Xaa Xaa Xaa Leu Xaa Tyr Asp Ile Thr Asn Xaa Xaa Ser
                 85                  90                  95

Phe Asp Asn Ile Arg Xaa Trp Xaa Xaa Xaa Ile Xaa Glu Xaa Ala Xaa
                100                 105                 110

Xaa Asp Val Xaa Xaa Met Xaa Leu Gly Asn Lys Xaa Asp Val Xaa Xaa
             115                 120                 125

Xaa Arg Xaa Xaa Xaa Xaa Glu Xaa Gly Glu Xaa Leu Ala Xaa Xaa Tyr
     130                 135                 140

Gly Xaa Xaa Phe Met Glu Thr Ser Ala Lys Xaa Xaa Xaa Asn Val Glu
145                 150                 155                 160

Xaa Ala Phe Xaa Xaa Xaa Ala Xaa Xaa Xaa Lys Xaa Xaa Xaa Xaa Xaa
                165                 170                 175

Xaa Xaa Xaa Xaa Xaa Xaa Xaa Xaa Xaa Xaa Xaa Val Xaa Xaa Xaa
            180                 185                 190

Xaa Xaa Xaa Xaa Xaa Xaa Xaa Ser Phe Xaa Xaa
            195                 200

<210> SEQ ID NO 14
<211> LENGTH: 216
<212> TYPE: PRT
<213> ORGANISM: Rat

<400> SEQUENCE: 14

Ala Thr Ala Gly Asp Glu Ala Pro Glu Arg Arg Ser Pro Pro Phe Ser
  1               5                  10                  15

Pro Asn Tyr Asp Leu Thr Gly Lys Val Met Leu Leu Gly Asp Ser Gly
             20                  25                  30

Val Gly Lys Thr Cys Phe Leu Ile Gln Phe Lys Asp Gly Ala Phe Leu
         35                  40                  45
```

-continued

```
Ser Gly Thr Phe Ile Ala Thr Val Gly Ile Asp Phe Arg Asn Lys Val
         50                  55                  60

Val Thr Val Asp Gly Ala Arg Val Lys Leu Gln Ile Trp Asp Thr Ala
 65                  70                  75                  80

Gly Gln Glu Arg Phe Arg Ser Val Thr His Ala Tyr Tyr Arg Asp Ala
                 85                  90                  95

Gln Ala Leu Leu Leu Leu Tyr Asp Ile Thr Asn Gln Ser Ser Phe Asp
                100                 105                 110

Asn Ile Arg Ala Trp Leu Thr Glu Ile His Glu Tyr Ala Gln Arg Asp
            115                 120                 125

Val Val Ile Met Leu Leu Gly Asn Lys Ala Asp Val Ser Ser Glu Arg
        130                 135                 140

Val Ile Arg Ser Glu Asp Gly Glu Thr Leu Ala Arg Glu Tyr Gly Val
145                 150                 155                 160

Pro Phe Met Glu Thr Ser Ala Lys Thr Gly Met Asn Val Glu Leu Ala
                165                 170                 175

Phe Leu Ala Ile Ala Lys Glu Leu Lys Tyr Arg Ala Gly Arg Gln Pro
            180                 185                 190

Asp Glu Pro Ser Phe Gln Ile Arg Asp Tyr Val Glu Ser Gln Lys Lys
        195                 200                 205

Arg Ser Ser Cys Cys Ser Phe Val
    210                 215
```

<210> SEQ ID NO 15
<211> LENGTH: 217
<212> TYPE: PRT
<213> ORGANISM: Homo sapiens
<220> FEATURE:
<221> NAME/KEY: UNSURE
<222> LOCATION: (48)
<223> OTHER INFORMATION: The xaa at position 48 represents an unknown
      amino acid.

<400> SEQUENCE: 15

```
Met Ala Ser Ala Thr Asp Ser Arg Tyr Gly Gln Lys Glu Ser Ser Asp
  1               5                  10                  15

Gln Asn Phe Asp Tyr Met Phe Lys Ile Leu Ile Ile Gly Asn Ser Ser
                 20                  25                  30

Val Gly Lys Thr Ser Phe Leu Phe Arg Tyr Ala Asp Asp Ser Phe Xaa
             35                  40                  45

Thr Pro Ala Phe Val Ser Thr Val Gly Ile Asp Phe Lys Val Lys Thr
 50                  55                  60

Ile Tyr Arg Asn Asp Lys Arg Ile Lys Leu Gln Ile Trp Asp Thr Ala
 65                  70                  75                  80

Gly Gln Glu Arg Tyr Arg Thr Ile Thr Thr Ala Tyr Tyr Arg Gly Ala
                 85                  90                  95

Met Gly Phe Ile Leu Met Tyr Asp Ile Thr Asn Glu Glu Ser Phe Asn
            100                 105                 110

Ala Val Gln Asp Trp Ser Thr Gln Ile Lys Thr Tyr Ser Trp Asp Asn
        115                 120                 125

Ala Gln Val Leu Leu Val Gly Asn Lys Cys Asp Met Glu Asp Glu Arg
    130                 135                 140

Val Val Ser Ser Glu Arg Gly Arg Gln Leu Ala Asp His Leu Gly Phe
145                 150                 155                 160

Glu Phe Phe Glu Ala Ser Ala Lys Asp Asn Ile Asn Val Lys Gln Thr
                165                 170                 175
```

```
Phe Glu Arg Leu Val Asp Val Ile Cys Glu Lys Met Ser Glu Ser Leu
            180                 185                 190

Asp Thr Ala Asp Pro Ala Val Thr Gly Ala Lys Gln Gly Pro Gln Leu
        195                 200                 205

Ser Asp Gln Gln Val Pro Pro His Gln
    210                 215

<210> SEQ ID NO 16
<211> LENGTH: 217
<212> TYPE: PRT
<213> ORGANISM: Artificial Sequence
<220> FEATURE:
<223> OTHER INFORMATION: Description of Artificial Sequence:  Consensus
<221> NAME/KEY: UNSURE
<222> LOCATION: (1)
<223> OTHER INFORMATION: The xaa at position 1 represents a non-
      conserved amino acid.
<221> NAME/KEY: UNSURE
<222> LOCATION: (2)
<223> OTHER INFORMATION: The xaa at position 2 represents either
      Threonine or Alanine.
<221> NAME/KEY: UNSURE
<222> LOCATION: (3)
<223> OTHER INFORMATION: The xaa at position 3 represents either Alanine
      or Serine.
<221> NAME/KEY: UNSURE
<222> LOCATION: (4)
<223> OTHER INFORMATION: The xaa at position 4 represents either Glycine
      or Alanine.
<221> NAME/KEY: UNSURE
<222> LOCATION: (5)
<223> OTHER INFORMATION: The xaa at position 5 represents either
      Aspartic acid or Threonine.
<221> NAME/KEY: UNSURE
<222> LOCATION: (6)
<223> OTHER INFORMATION: The xaa at position 6 represents either Glycine
      or Aspartic acid.
<221> NAME/KEY: UNSURE
<222> LOCATION: (7)
<223> OTHER INFORMATION: The xaa at position 7 represents either
      Glutamic acid or Serine.
<221> NAME/KEY: UNSURE
<222> LOCATION: (8)
<223> OTHER INFORMATION: The xaa at position 8 represents a non-
      conserved amino acid.
<221> NAME/KEY: UNSURE
<222> LOCATION: (9)
<223> OTHER INFORMATION: The xaa at position 9 represents a non-
      conserved amino acid.
<221> NAME/KEY: UNSURE
<222> LOCATION: (10)
<223> OTHER INFORMATION: The xaa at position 10 represents either
      Glutamic acid or Glycine.
<221> NAME/KEY: UNSURE
<222> LOCATION: (11)
<223> OTHER INFORMATION: The xaa at position 11 represents either
      Arginine or Glutamine.
<221> NAME/KEY: UNSURE
<222> LOCATION: (12)
<223> OTHER INFORMATION: The xaa at position 12 represents either Serine
      or Lycine.
<221> NAME/KEY: UNSURE
<222> LOCATION: (13)
<223> OTHER INFORMATION: The xaa at position 13 represents a non-
      conserved amino acid.
<221> NAME/KEY: UNSURE
<222> LOCATION: (14)
<223> OTHER INFORMATION: The xaa at position 14 represents either
      Proline or Serine.
<221> NAME/KEY: UNSURE
<222> LOCATION: (15)
<223> OTHER INFORMATION: The xaa at position 15 represents a non-
      conserved amino acid.
<221> NAME/KEY: UNSURE
<222> LOCATION: (16)
```

-continued

```
<223> OTHER INFORMATION: The xaa at position 16 represents either Serine
      or Aspartic acid.
<221> NAME/KEY: UNSURE
<222> LOCATION: (17)
<223> OTHER INFORMATION: The xaa at position 17 represents either
      Proline or Glutamine.
<221> NAME/KEY: UNSURE
<222> LOCATION: (19)
<223> OTHER INFORMATION: The xaa at postion 19 represents either
      Tyrosine or Phenylalanine.
<221> NAME/KEY: UNSURE
<222> LOCATION: (21)..(23)
<223> OTHER INFORMATION: The xaa at positions 21 through 23 represents
      a non-conserved amino acid.
<221> NAME/KEY: UNSURE
<222> LOCATION: (25)
<223> OTHER INFORMATION: The xaa at position 25 represents Valine or
      Isoleucine.
<221> NAME/KEY: UNSURE
<222> LOCATION: (26)
<223> OTHER INFORMATION: The xaa at position 26 represents either
      Methionine or Leucine.
<221> NAME/KEY: UNSURE
<222> LOCATION: (27)..(28)
<223> OTHER INFORMATION: The xaa at position 27 and 28 represents
      Leucine or Isoleucine.
<221> NAME/KEY: UNSURE
<222> LOCATION: (30)
<223> OTHER INFORMATION: The xaa at position 30 represents either
      Aspartic acid or Asparagine.
<221> NAME/KEY: UNSURE
<222> LOCATION: (32)
<223> OTHER INFORMATION: The xaa at position 32 represents either
      Glycine or Serine.
<221> NAME/KEY: UNSURE
<222> LOCATION: (37)
<223> OTHER INFORMATION: The xaa at position 37 represents Cysteine or
      Serine.
<221> NAME/KEY: UNSURE
<222> LOCATION: (40)
<223> OTHER INFORMATION: The xaa at position 40 represents either
      Isoleucine or Phenylalanine.
<221> NAME/KEY: UNSURE
<222> LOCATION: (41)
<223> OTHER INFORMATION: The xaa at position 41 represents either
      Glutamine or Arginine.
<221> NAME/KEY: UNSURE
<222> LOCATION: (42)
<223> OTHER INFORMATION: The xaa at position 42 represents either
      Phenylalanine or Tyrosine.
<221> NAME/KEY: UNSURE
<222> LOCATION: (43)
<223> OTHER INFORMATION: The xaa at position 43 represents a non-
      conserved amino acid.
<221> NAME/KEY: UNSURE
<222> LOCATION: (45)
<223> OTHER INFORMATION: The xaa at position 45 represents either
      Glycine or Aspartic acid.
<221> NAME/KEY: UNSURE
<222> LOCATION: (46)
<223> OTHER INFORMATION: The xaa at position 46 represents either
      Alanine or Serine.
<221> NAME/KEY: UNSURE
<222> LOCATION: (48)
<223> OTHER INFORMATION: The xaa at position 48 represents a non-
      conserved amino acid.
<221> NAME/KEY: UNSURE
<222> LOCATION: (49)
<223> OTHER INFORMATION: The xaa at position 49 represents either Serine
      or Threonine.
<221> NAME/KEY: UNSURE
<222> LOCATION: (50)
<223> OTHER INFORMATION: The xaa at position 50 represents a non-
      conserved amino acid.
<221> NAME/KEY: UNSURE
<222> LOCATION: (51)
<223> OTHER INFORMATION: The xaa at position 51 represents either
      Threonine or Alanine.
<221> NAME/KEY: UNSURE
```

```
<222> LOCATION: (53)
<223> OTHER INFORMATION: The xaa at position 53 represents Threonine or
      Valine.
<221> NAME/KEY: UNSURE
<222> LOCATION: (54)
<223> OTHER INFORMATION: The xaa at position 54 represents either
      Alanine or Serine.
<221> NAME/KEY: UNSURE
<222> LOCATION: (61)
<223> OTHER INFORMATION: The xaa at position 61 represents either
      Arginine or Lysine.
<221> NAME/KEY: UNSURE
<222> LOCATION: (62)
<223> OTHER INFORMATION: The xaa at position 62 represents a non-
      conserved amino acid.
<221> NAME/KEY: UNSURE
<222> LOCATION: (64)
<223> OTHER INFORMATION: The xaa at position 64 represents either Valine
      or Threonine.
<221> NAME/KEY: UNSURE
<222> LOCATION: (65)
<223> OTHER INFORMATION: The xaa at position 65 represents either Valine
      Isoleucine.
<221> NAME/KEY: UNSURE
<222> LOCATION: (66)..(67)
<223> OTHER INFORMATION: The xaa at positions 66 and 67 represents a
      non-conserved amino acid.
<221> NAME/KEY: UNSURE
<222> LOCATION: (68)
<223> OTHER INFORMATION: The xaa at position 68 represents either
      Aspartic acid or Asparagine.
<221> NAME/KEY: UNSURE
<222> LOCATION: (69)
<223> OTHER INFORMATION: The xaa at position 69 represents either
      Glycine or Aspartic acid.
<221> NAME/KEY: UNSURE
<222> LOCATION: (70)
<223> OTHER INFORMATION: The xaa at position 70 represents a non-
      conserved amino acid.
<221> NAME/KEY: UNSURE
<222> LOCATION: (72)
<223> OTHER INFORMATION: The xaa at position 72 represents either Valine
      or Isoleucine.
<221> NAME/KEY: UNSURE
<222> LOCATION: (85)
<223> OTHER INFORMATION: The xaa at position 85 represents either
      Phenyalanine or Tyrosine.
<221> NAME/KEY: UNSURE
<222> LOCATION: (87)
<223> OTHER INFORMATION: The xaa at position 87 represents either Serine
      or Threonine.
<221> NAME/KEY: UNSURE
<222> LOCATION: (88)
<223> OTHER INFORMATION: The xaa at position 88 represents either Valine
      or Threonine.
<221> NAME/KEY: UNSURE
<222> LOCATION: (90)
<223> OTHER INFORMATION: The xaa at position 90 represents a non-
      conserved amino acid.
<221> NAME/KEY: UNSURE
<222> LOCATION: (95)
<223> OTHER INFORMATION: The xaa at position 95 represents either
      Aspartic acid or Glycine.
<221> NAME/KEY: UNSURE
<222> LOCATION: (97)
<223> OTHER INFORMATION: The xaa at position 97 represents a non-
      conserved amino acid.
<221> NAME/KEY: UNSURE
<222> LOCATION: (98)
<223> OTHER INFORMATION: The xaa at position 98 represents either
      Arginine or Glycine.
<221> NAME/KEY: UNSURE
<222> LOCATION: (99)
<223> OTHER INFORMATION: The xaa at position 99 represents either
      Leucine or Phenylanine.
<221> NAME/KEY: UNSURE
<222> LOCATION: (100)
<223> OTHER INFORMATION: The xaa at position 100 represents either
      Leucine or Isoleucine.
```

```
<221> NAME/KEY: UNSURE
<222> LOCATION: (102)
<223> OTHER INFORMATION: The xaa at position 102 represents either
      Leucine or Methionine.
<221> NAME/KEY: UNSURE
<222> LOCATION: (108)
<223> OTHER INFORMATION: The xaa at position 108 represents either
      Glutamine or Glutamic acid.
<221> NAME/KEY: UNSURE
<222> LOCATION: (109)
<223> OTHER INFORMATION: The xaa at position 109 represents either
      Serine or Glutamic acid.
<221> NAME/KEY: UNSURE
<222> LOCATION: (112)
<223> OTHER INFORMATION: The xaa at position 112 represents either
      Aspartic acid or Asparagine.
<221> NAME/KEY: UNSURE
<222> LOCATION: (113)
<223> OTHER INFORMATION: The xaa at position 113 represents a non-
      conserved amino acid.
<221> NAME/KEY: UNSURE
<222> LOCATION: (114)
<223> OTHER INFORMATION: The xaa at position 114 represents either
      Isoleucine or Tyrosine.
<221> NAME/KEY: UNSURE
<222> LOCATION: (115)
<223> OTHER INFORMATION: The xaa at position 115 represents either
      Arginine or Glutamine.
<221> NAME/KEY: UNSURE
<222> LOCATION: (116)
<223> OTHER INFORMATION: The xaa at position 116 represents either
      Arginine or Aspartic acid.
<221> NAME/KEY: UNSURE
<222> LOCATION: (118)
<223> OTHER INFORMATION: The xaa at position 118 represents either
      Leucine or Serine.
<221> NAME/KEY: UNSURE
<222> LOCATION: (120)
<223> OTHER INFORMATION: The xaa at position 120 represents either
      Glutamic acid or Glutamine.
<221> NAME/KEY: UNSURE
<222> LOCATION: (122)
<223> OTHER INFORMATION: The xaa at position 122 represents either
      Histidine or Lysine.
<221> NAME/KEY: UNSURE
<222> LOCATION: (123)
<223> OTHER INFORMATION: The xaa at position 123 represents either
      Glutamic acid or Threonine.
<221> NAME/KEY: UNSURE
<222> LOCATION: (125)
<223> OTHER INFORMATION: The xaa at position 125 represents either
      Alanine or Serine.
<221> NAME/KEY: UNSURE
<222> LOCATION: (126)..(127)
<223> OTHER INFORMATION: The xaa at position 126 through 127 represents
      a non-conserved amino acid.
<221> NAME/KEY: UNSURE
<222> LOCATION: (128)
<223> OTHER INFORMATION: The xaa at position 128 represents either
      Aspartic acid or Arginine.
<221> NAME/KEY: UNSURE
<222> LOCATION: (129)
<223> OTHER INFORMATION: The xaa at position 129 represents either
      Valine or Alanine.
<221> NAME/KEY: UNSURE
<222> LOCATION: (130)
<223> OTHER INFORMATION: The xaa at position 130 represents a non-
      conserved amino acid.
<221> NAME/KEY: UNSURE
<222> LOCATION: (131)
<223> OTHER INFORMATION: The xaa at position 131 represents either
      Isoleucine or Valine.
<221> NAME/KEY: UNSURE
<222> LOCATION: (132)
<223> OTHER INFORMATION: The xaa at position 132 represents either
      Methionine or Leucine.
<221> NAME/KEY: UNSURE
<222> LOCATION: (134)
<223> OTHER INFORMATION: The xaa at position 134 represents either
```

```
         Leucine or Valine.
<221>  NAME/KEY: UNSURE
<222>  LOCATION: (138)
<223>  OTHER INFORMATION: The xaa at position 138 represents either
       Alanine or Cysteine.
<221>  NAME/KEY: UNSURE
<222>  LOCATION: (140)
<223>  OTHER INFORMATION: The xaa at position 140 represents either
       Valine or Methionine.
<221>  NAME/KEY: UNSURE
<222>  LOCATION: (141)
<223>  OTHER INFORMATION: The xaa at position 141 represents either
       Serine or Glutamic acid.
<221>  NAME/KEY: UNSURE
<222>  LOCATION: (142)
<223>  OTHER INFORMATION: The xaa at position 142 represents either
       Serine or Aspartic acid.
<221>  NAME/KEY: UNSURE
<222>  LOCATION: (146)
<223>  OTHER INFORMATION: The xaa at position 146 represents either
       Isoleucine or Valine.
<221>  NAME/KEY: UNSURE
<222>  LOCATION: (147)
<223>  OTHER INFORMATION: The xaa at position 147 represents either
       Asparagine or Serine.
<221>  NAME/KEY: UNSURE
<222>  LOCATION: (150)
<223>  OTHER INFORMATION: The xaa at position 150 represents either
       Aspartic acid or Arginine.
<221>  NAME/KEY: UNSURE
<222>  LOCATION: (152)
<223>  OTHER INFORMATION: The xaa at position 152 represents either
       Glutamic acid or Arginine.
<221>  NAME/KEY: UNSURE
<222>  LOCATION: (153)
<223>  OTHER INFORMATION: The xaa at position 153 represents either
       Threonine or Glutamine.
<221>  NAME/KEY: UNSURE
<222>  LOCATION: (156)
<223>  OTHER INFORMATION: The xaa at position 156 represents a non-
       conserved amino acid.
<221>  NAME/KEY: UNSURE
<222>  LOCATION: (157)
<223>  OTHER INFORMATION: The xaa at position 157 represents either
       Glutamic acid or Histidine.
<221>  NAME/KEY: UNSURE
<222>  LOCATION: (158)
<223>  OTHER INFORMATION: The xaa at position 158 represents a non-
       conserved amino acid.
<221>  NAME/KEY: UNSURE
<222>  LOCATION: (160)..(161)
<223>  OTHER INFORMATION: The xaa at positions 160 and 161 represents a
       non-conserved amino acid.
<221>  NAME/KEY: UNSURE
<222>  LOCATION: (163)
<223>  OTHER INFORMATION: The xaa at position 163 represents either
       Methionine or Phenylanine.
<221>  NAME/KEY: UNSURE
<222>  LOCATION: (165)
<223>  OTHER INFORMATION: The xaa at position 165 represents either
       Threonine or Alanine.
<221>  NAME/KEY: UNSURE
<222>  LOCATION: (169)
<223>  OTHER INFORMATION: The xaa at position 169 represents either
       Threonine or Aspartic acid.
<221>  NAME/KEY: UNSURE
<222>  LOCATION: (170)
<223>  OTHER INFORMATION: The xaa at position 170 represents either
       Glycine or Asparagine.
<221>  NAME/KEY: UNSURE
<222>  LOCATION: (171)
<223>  OTHER INFORMATION: The xaa at position 171 represents either
       Methionine or Isoleucine.
<221>  NAME/KEY: UNSURE
<222>  LOCATION: (174)
<223>  OTHER INFORMATION: The xaa at position 174 represents either
       Glutamic acid or Lysine.
<221>  NAME/KEY: UNSURE
<222>  LOCATION: (175)
```

-continued

```
<223> OTHER INFORMATION: The xaa at position 175 represents a non-
      conserved amino acid.
<221> NAME/KEY: UNSURE
<222> LOCATION: (176)
<223> OTHER INFORMATION: The xaa at position 176 represents either
      Alanine or Threonine.
<221> NAME/KEY: UNSURE
<222> LOCATION: (178)..(179)
<223> OTHER INFORMATION: The xaa at positions 178 and 179 represents a
      non-conserved amino acid.
<221> NAME/KEY: UNSURE
<222> LOCATION: (180)
<223> OTHER INFORMATION: The xaa at position 180 represents either
      Isoleucine or Leucine.
<221> NAME/KEY: UNSURE
<222> LOCATION: (181)
<223> OTHER INFORMATION: The xaa at position 181 represents either
      Alanine or Valine.
<221> NAME/KEY: UNSURE
<222> LOCATION: (182)
<223> OTHER INFORMATION: The xaa at position 182 represents either
      Lysine or Aspartic acid.
<221> NAME/KEY: UNSURE
<222> LOCATION: (183)
<223> OTHER INFORMATION: The xaa at position 183 represents a non-
      conserved amino acid.
<221> NAME/KEY: UNSURE
<222> LOCATION: (184)
<223> OTHER INFORMATION: The xaa at position 184 represents either
      Leucine or Isoleucine.
<221> NAME/KEY: UNSURE
<222> LOCATION: (185)..(186)
<223> OTHER INFORMATION: The xaa at positions 185 and 186 represents
      a non-conserved amino acid.
<221> NAME/KEY: UNSURE
<222> LOCATION: (187)
<223> OTHER INFORMATION: The xaa at position 187 represents either
      Arginine or Lysine.
<221> NAME/KEY: UNSURE
<222> LOCATION: (188)
<223> OTHER INFORMATION: The xaa at position 188 represents a non-
      conserved amino acid.
<221> NAME/KEY: UNSURE
<222> LOCATION: (189)
<223> OTHER INFORMATION: The xaa at position 189 represents either
      Glycine or Serine.
<221> NAME/KEY: UNSURE
<222> LOCATION: (190)..(192)
<223> OTHER INFORMATION: The xaa at positions 190 through 192 represents
      a non-conserved amino acid.
<221> NAME/KEY: UNSURE
<222> LOCATION: (194)
<223> OTHER INFORMATION: The xaa at position 194 represents either
      Glutamic acid or Threonine.
<221> NAME/KEY: UNSURE
<222> LOCATION: (195)
<223> OTHER INFORMATION: The xaa at position 195 represents either
      Phenylalanine or Alanine.
<221> NAME/KEY: UNSURE
<222> LOCATION: (196)
<223> OTHER INFORMATION: The xaa at position 196 represents either
      Serine or Aspartic acid.
<221> NAME/KEY: UNSURE
<222> LOCATION: (197)
<223> OTHER INFORMATION: The xaa at position 197 represents a non-
      conserved amino acid.
<221> NAME/KEY: UNSURE
<222> LOCATION: (198)
<223> OTHER INFORMATION: The xaa at position 198 represents either
      Glutamine or Alanine.
<221> NAME/KEY: UNSURE
<222> LOCATION: (199)
<223> OTHER INFORMATION: The xaa at position 199 represents either
      Isoleucine or Valine.
<221> NAME/KEY: UNSURE
<222> LOCATION: (200)
<223> OTHER INFORMATION: The xaa at position 200 represents a non-
      conserved amino acid.
<221> NAME/KEY: UNSURE
```

<222> LOCATION: (201)
<223> OTHER INFORMATION: The xaa at position 201 represents either
      Aspartic acid or Glycine.
<221> NAME/KEY: UNSURE
<222> LOCATION: (202)..(203)
<223> OTHER INFORMATION: The xaa at position 202 and 203 represents a
      non-conserved amino acid.
<221> NAME/KEY: UNSURE
<222> LOCATION: (204)
<223> OTHER INFORMATION: The xaa at position 204 represents either
      Glutamic acid or Glutamine.
<221> NAME/KEY: UNSURE
<222> LOCATION: (205)
<223> OTHER INFORMATION: The xaa at position 205 represents either
      Serine or Glycine.
<221> NAME/KEY: UNSURE
<222> LOCATION: (206)
<223> OTHER INFORMATION: The xaa at position 206 represents either
      Glutamine or Proline.
<221> NAME/KEY: UNSURE
<222> LOCATION: (207)
<223> OTHER INFORMATION: The xaa at position 207 represents either
      Lycine or Glutamine.
<221> NAME/KEY: UNSURE
<222> LOCATION: (208)
<223> OTHER INFORMATION: The xaa at position 208 represents a non-
      conserved amino acid.
<221> NAME/KEY: UNSURE
<222> LOCATION: (209)
<223> OTHER INFORMATION: The xaa at position 209 represents either
      Arginine or Serine.
<221> NAME/KEY: UNSURE
<222> LOCATION: (210)
<223> OTHER INFORMATION: The xaa at position 210 represents either
      Serine or Aspartic acid.
<221> NAME/KEY: UNSURE
<222> LOCATION: (211)..(213)
<223> OTHER INFORMATION: The xaa at positions 211 through 213 represents
      a non-conserved amino acid.
<221> NAME/KEY: UNSURE
<222> LOCATION: (214)
<223> OTHER INFORMATION: The xaa at position 214 represents either
      Serine or Proline.
<221> NAME/KEY: UNSURE
<222> LOCATION: (215)
<223> OTHER INFORMATION: The xaa at position 215 represents either
      Phenylanine or Proline.
<221> NAME/KEY: UNSURE
<222> LOCATION: (216)
<223> OTHER INFORMATION: The xaa at position 216 represents either
      Valine or Histidine.
<221> NAME/KEY: UNSURE
<222> LOCATION: (217)
<223> OTHER INFORMATION: The xaa at position 217 represents either
      Glutamine or no amino acid.

<400> SEQUENCE: 16

Xaa Xaa Xaa Xaa Xaa Xaa Xaa Xaa Xaa Xaa Xaa Xaa Xaa Xaa Xaa Xaa
 1               5                   10                  15

Xaa Asn Xaa Asp Xaa Xaa Xaa Lys Xaa Xaa Xaa Gly Xaa Ser Xaa
             20                  25                  30

Val Gly Lys Thr Xaa Phe Leu Xaa Xaa Xaa Asp Xaa Xaa Phe Xaa
         35                  40                  45

Xaa Xaa Xaa Phe Xaa Xaa Thr Val Gly Ile Asp Phe Xaa Xaa Lys Xaa
     50                  55                  60

Xaa Xaa Xaa Xaa Xaa Xaa Arg Xaa Lys Leu Gln Ile Trp Asp Thr Ala
 65                  70                  75                  80

Gly Gln Glu Arg Xaa Arg Xaa Xaa Thr Xaa Ala Tyr Tyr Arg Xaa Ala
                 85                  90                  95

Xaa Xaa Xaa Xaa Leu Xaa Tyr Asp Ile Thr Asn Xaa Xaa Ser Phe Xaa
             100                 105                 110

-continued

```
Xaa Xaa Xaa Xaa Trp Xaa Thr Xaa Ile Xaa Xaa Tyr Xaa Xaa Xaa Xaa
        115                 120                 125

Xaa Xaa Xaa Xaa Leu Xaa Gly Asn Lys Xaa Asp Xaa Xaa Xaa Glu Arg
    130                 135                 140

Val Xaa Xaa Ser Glu Xaa Gly Xaa Xaa Leu Ala Xaa Xaa Xaa Gly Xaa
145                 150                 155                 160

Xaa Phe Xaa Glu Xaa Ser Ala Lys Xaa Xaa Xaa Asn Val Xaa Xaa Xaa
                165                 170                 175

Phe Xaa Xaa Xaa Xaa Xaa Xaa Xaa Xaa Xaa Xaa Xaa Xaa Xaa Xaa Xaa
            180                 185                 190

Asp Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa
    210                 215
```